(12) United States Patent
Sheffield et al.

(10) Patent No.: US 8,129,161 B2
(45) Date of Patent: *Mar. 6, 2012

(54) BARDET-BIEDL SUSCEPTIBILITY GENE AND USES THEREOF

(75) Inventors: Val Sheffield, Iowa City, IA (US); Darryl Nishimura, Coralville, IA (US); Edwin Stone, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/908,707

(22) Filed: Oct. 20, 2010

(65) Prior Publication Data

US 2011/0033921 A1 Feb. 10, 2011

Related U.S. Application Data

(60) Continuation of application No. 11/370,242, filed on Mar. 7, 2006, which is a division of application No. 10/025,187, filed on Dec. 18, 2001, now Pat. No. 7,008,782.

(60) Provisional application No. 60/256,900, filed on Dec. 19, 2000, provisional application No. 60/258,949, filed on Dec. 29, 2000.

(51) Int. Cl.
*C12N 15/63* (2006.01)

(52) U.S. Cl. ............. 435/183; 435/320.1; 536/23.5

(58) Field of Classification Search .............. None
See application file for complete search history.

(56) References Cited

U.S. PATENT DOCUMENTS

| 4,988,617 A | 1/1991 | Landegren et al. ........... 435/6 |
| 7,947,479 B2 * | 5/2011 | Sheffield et al. ............ 435/183 |
| 2006/0205052 A1 * | 9/2006 | Sheffield et al. ............ 435/183 |

FOREIGN PATENT DOCUMENTS

| EP | 1074617 | 4/2004 |
| WO | WO 00/35937 | 6/2000 |
| WO | WO 01/00825 | 1/2001 |
| WO | WO 02/50309 | 6/2002 |

OTHER PUBLICATIONS

Bruford et al., "Linkage mapping in 29 Bardet-Biedl syndrome families confirms loci in chromosomal regions 11q13, 15q22.3-q23, and 16q21," *Genomics*, 41:93-99, 1997.
Carmi et al., "Phenotypic differences among patients with Bardet-Biedl syndrome linked to three different chromosome loci," *Am. J. Med. Genet.*, 59:199-203, 1995.
Carmi et al., "Use of a DNA pooling strategy to identify a human obesity syndrome locus on chromosome 15," *Hum. Mol. Genet.*, 4:9-13, 1995.
Farag and Teebi, "Bardet-Biedl and Laurence-Moon syndromes in a mixed Arab population," *Clinical Genet.*, 33:78-82, 1988.
Farag and Teebi, "High incidence of Bardet Biedl syndrome among the Bedouin [letter]," *Clinical Genet.*, 36:463-464, 1989.
Hoang et al., "Cloning of a novel c-terminal kinesin (KIFC3) that maps to human chromosome 16Q13-Q21 and thus is a candidate gene for Bardet-Biedl syndrome," *Genomics*,52:219-222, 1998.
Katsanis et al., "Mutations in MKKS cause obesity, retinal dystrophy and renal malformations associated with bardet-biedl syndrome," *Nat. Genet.*, 26:67-70, 2000.
Kwitek-Black et al., "Linkage of Bardet-Biedl syndrome to chromosome 16q and evidence for non-allelic genetic heterogeneity," *Nature Genet.*, 5:392-396, 1993.
Leppert et al., "Bardet-Biedl syndrome is linked to DNA markers on chromosome 11q and is genetically heterogeneous," *Nature Genet.*, 7:108-112, 1994.
Nishimura et al., "The forkhead transcription factor gene FKHL7 is responsible for glaucoma phenotypes which map to 6p25," *Nature Genet.*, 19:140-147, 1998.
Office Communication, issued in U.S. Appl. No. 10/025,187, dated Sep. 23, 2003.
Office Communication, issued in U.S. Appl. No. 10/025,187, dated Jul. 28, 2004.
Office Communication, issued in U.S. Appl. No. 10/025,187, dated Jan. 11, 2005.
Office Communication, issued in U.S. Appl. No. 11/370,242, dated May 16, 2008.
Office Communication, issued in U.S. Appl. No. 11/370,242, dated Feb. 5, 2009.
Office Communication, issued in U.S. Appl. No. 11/370,242, dated Jul. 23, 2009.
Office Communication, issued in U.S. Appl. No. 11/370,242, dated Jun. 18, 2010.
Sheffield et al., "Identification of a Bardet-Biedl syndrome locus on chromosome 3 and evaluation of an efficient approach to homozygosity mapping," *Hum. Mol. Genet.*, 3(8):1331-1335, 1994.
Slavotinek et al., "Mutations in MKKS cause bardet-biedl syndrome," *Nature Genet.*, 26:15-16, 2000.
Stone et al., "Mutation of a gene encoding a putative chaperonin causes McKusick-Kaufman syndrome," *Nat. Genet.*, 25:79-82, 2000.
Swiderski et al., "Expression pattern and in situ localization of the mouse homologue of the human MYCO (GLC1A) gene in adult brain," *Mol. Brain Res.*, 68:64-72, 1999.
Woods et al., "Genetic heterogeneity of Bardet-Biedl syndrome in a distinct Canadian population: evidence for a fifth locus," *Genomics*, 55:2-9, 1999.
Young et al., "A fifth locus for Bardet-Biedl syndrome maps to chromosome 2q31," *Am. J. Hum. Genet.*, 64:900-904, 1999.

* cited by examiner

*Primary Examiner* — Christopher R. Tate
*Assistant Examiner* — Roy Teller
(74) *Attorney, Agent, or Firm* — Fulbright & Jaworski

(57) ABSTRACT

The present invention relates to the identification of a gene, now designated negevin (ngvn), that is involved in the genetic disease Bardet Biedl Syndrome (BBS), which is characterized by such diverse symptoms as obesity, diabetes, hypertension, mental retardation, renal cancer and other abnormalities, retinopathy and hypogonadism. The human NGVN protein disclosed herein is 731 amino acids in length and is coded for by a gene spanning 17 exons. Homologs have been identified in mouse, rat, zebrafish. Methods of use for the gene, for example in diagnosis and therapy of BBS and in drug screening, also are described.

15 Claims, No Drawings

SEQUENCE LISTING

```
<160> NUMBER OF SEQ ID NOS: 3

<210> SEQ ID NO 1
<211> LENGTH: 2166
<212> TYPE: DNA
<213> ORGANISM: Homo sapiens

<400> SEQUENCE: 1
atgctgctgc ctgtgttcac cctgaaactg cgccacaaaa tcagcccccg aatggtggcc      60 ataggcgct acgacgggac tcacccgtgc ctggcggccg ccacccaaac gggcaaggtt     120
tttattcata atcctcatac acggaaccag catgtcagtg catccagggt cttccagagc     180 ccctggaat ctgatgtttc tcttctcaac attaaccagg cagtcagctg tctgactgca     240
ggcgtattga accctgagct tggctatgat gccctttag tggggacaca gactaatctt     300
ttggcttatg atgtctacaa taattcggat ttgttctaca gagaggtagc agatgggca     360 aatgcaattg tgctggggac attgggagac atttcttccc ctcttgcgat tattggtggc     420 aattgtgtc tgcaaggttt caatcatgaa ggaagtgatc tcttttggac ggttactgga     480
gacaatgtta attccttggc cttgtgtgac tttgatggtg atggaaagaa agagcttctt     540
gttggatctg aggattttga tatccgagtt tttaaggaag atgagattgt ggcagaaatg     600
acagaaacag agatagtcac ctctctttgt cccatgtatg gcagtcgatt tggttatgcc     660
ctttccaatg gcacagttgg agtttatgac aaaacatccc gatactggag aattaaatcg     720
aaaaatcatg ccatgagcat tcatgctttt gaccttaatt ctgatggagt gaatgaactg     780
ataactggtt ggtccaatgg gaaggttgat gctcgaagtg accgaactgg ggaggtcatc     840
```

-continued

```
tttaaggaca attttctctc tgcaattgcc ggtgtggtag agggagatta ccggatggat      900
ggccacatac agttaatctg ctgctcagtg gatggggaaa tccggggcta cctgcctggc      960
acggctgaga tgaggggcaa cctcatggac accagtgcag agcaggacct gatccgagag     1020
ctgagtcaga agaagcagaa tctgttgctg aactccgta actatgagga aaatgccaag      1080
gctgaattgg ccagtccact gaacgaggct gatgggcatc gggcataat cccagccaat      1140
accaggctcc acaccacgct ctcagtcagc ctggggaatg agacccaaac tgctcataca     1200
gaattacgca tttccacttc taatgacacc atcatccgag cagtattgat ttttgcagaa     1260
ggaattttta caggtgaaag ccacgtggta catcccagca ttcacaacct ctccagttcc     1320
atctgcatcc ctattgtgcc tcccaaagat gtccctgtgg atctgcactt gaaggcattc     1380
gtgggttaca aagcagcac ccagtttcat gtatttgaat cgacaagaca gctccctcga      1440
ttctccatgt atgcgctgac cagcctggac cctgccagtg agccaatcag ttatgttaac     1500
tttaccattg cagaacgggc acagagggtt gttgtatggc tcggtcagaa ctttctgtta     1560
ccagaagaca ctcacattca gaatgctcca tttcaagtgt gtttcacatc tttacggaat     1620
ggcggccacc tgcatataaa aataaaactt agtggagaga tcactataaa tactgatgat     1680
attgatttgg ctggtgatat catccagtca atggcatcat tttttgctat tgaagacctt     1740
caagtagaag cggattttcc tgtctatttt gaggaattac gaaaggtgct agttaaggtg     1800
gatgaatatc attcagtgca tcagaagctc agtgctgata tggctgatca ttctaatttg     1860
atccgaagtt tgctggtcgg agctgaggat gctcgtctga tgagggacat gaaaacaatg     1920
aagagtcgtt atatggaact ctatgacctt aatagagact tgctaaatgg atataaaatt     1980
cgctgtaaca atcacacaga gctgttggga aacctcaaag cagtaaatca agcaattcaa     2040
agagcaggtc gtctgcgggt tggaaaacca agaaccagg tgatcactgc ttgtcgggat      2100
gcaattcgaa gcaataacat caacacactg ttcaaaatca tgcgagtggg gacagcttct     2160
tcctag                                                                2166
```

<210> SEQ ID NO 2
<211> LENGTH: 721
<212> TYPE: PRT
<213> ORGANISM: Homo sapiens

<400> SEQUENCE: 2

```
Met Leu Leu Pro Val Phe Thr Leu Lys Leu Arg His Lys Ile Ser Pro
  1               5                  10                  15

Arg Met Val Ala Ile Gly Arg Tyr Asp Gly Thr His Pro Cys Leu Ala
             20                  25                  30

Ala Ala Thr Gln Thr Gly Lys Val Phe Ile His Asn Pro His Thr Arg
         35                  40                  45

Asn Gln His Val Ser Ala Ser Arg Val Phe Gln Ser Pro Leu Glu Ser
     50                  55                  60

Asp Val Ser Leu Leu Asn Ile Asn Gln Ala Val Ser Cys Leu Thr Ala
 65                  70                  75                  80

Gly Val Leu Asn Pro Glu Leu Gly Tyr Asp Ala Leu Leu Val Gly Thr
                 85                  90                  95

Gln Thr Asn Leu Leu Ala Tyr Asp Val Tyr Asn Asn Ser Asp Leu Phe
            100                 105                 110

Tyr Arg Glu Val Ala Asp Gly Ala Asn Ala Ile Val Leu Gly Thr Leu
        115                 120                 125

Gly Asp Ile Ser Ser Pro Leu Ala Ile Ile Gly Gly Asn Cys Ala Leu
```

```
              130                 135                 140
Gln Gly Phe Asn His Glu Gly Ser Asp Leu Phe Trp Thr Val Thr Gly
145                 150                 155                 160

Asp Asn Val Asn Ser Leu Ala Leu Cys Asp Phe Asp Gly Asp Gly Lys
                165                 170                 175

Lys Glu Leu Leu Val Gly Ser Glu Asp Phe Asp Ile Arg Val Phe Lys
                180                 185                 190

Glu Asp Glu Ile Val Ala Glu Met Thr Glu Thr Glu Ile Val Thr Ser
                195                 200                 205

Leu Cys Pro Met Tyr Gly Ser Arg Phe Gly Tyr Ala Leu Ser Asn Gly
210                 215                 220

Thr Val Gly Val Tyr Asp Lys Thr Ser Arg Tyr Trp Arg Ile Lys Ser
225                 230                 235                 240

Lys Asn His Ala Met Ser Ile His Ala Phe Asp Leu Asn Ser Asp Gly
                245                 250                 255

Val Asn Glu Leu Ile Thr Gly Trp Ser Asn Gly Lys Val Asp Ala Arg
                260                 265                 270

Ser Asp Arg Thr Gly Glu Val Ile Phe Lys Asp Asn Phe Ser Ser Ala
                275                 280                 285

Ile Ala Gly Val Val Glu Gly Asp Tyr Arg Met Asp Gly His Ile Gln
290                 295                 300

Leu Ile Cys Cys Ser Val Asp Gly Glu Ile Arg Gly Tyr Leu Pro Gly
305                 310                 315                 320

Thr Ala Glu Met Arg Gly Asn Leu Met Asp Thr Ser Ala Glu Gln Asp
                325                 330                 335

Leu Ile Arg Glu Leu Ser Gln Lys Lys Gln Asn Leu Leu Glu Leu
                340                 345                 350

Arg Asn Tyr Glu Glu Asn Ala Lys Ala Glu Leu Ala Ser Pro Leu Asn
                355                 360                 365

Glu Ala Asp Gly His Arg Gly Ile Ile Pro Ala Asn Thr Arg Leu His
                370                 375                 380

Thr Thr Leu Ser Val Ser Leu Gly Asn Glu Thr Gln Thr Ala His Thr
385                 390                 395                 400

Glu Leu Arg Ile Ser Thr Ser Asn Asp Thr Ile Ile Arg Ala Val Leu
                405                 410                 415

Ile Phe Ala Glu Gly Ile Phe Thr Gly Glu Ser His Val Val His Pro
                420                 425                 430

Ser Ile His Asn Leu Ser Ser Ser Ile Cys Ile Pro Ile Val Pro Pro
                435                 440                 445

Lys Asp Val Pro Val Asp Leu His Leu Lys Ala Phe Val Gly Tyr Arg
450                 455                 460

Ser Ser Thr Gln Phe His Val Phe Glu Ser Thr Arg Gln Leu Pro Arg
465                 470                 475                 480

Phe Ser Met Tyr Ala Leu Thr Ser Leu Asp Pro Ala Ser Glu Pro Ile
                485                 490                 495

Ser Tyr Val Asn Phe Thr Ile Ala Glu Arg Ala Gln Arg Val Val Val
                500                 505                 510

Trp Leu Gly Gln Asn Phe Leu Leu Pro Glu Asp Thr His Ile Gln Asn
                515                 520                 525

Ala Pro Phe Gln Val Cys Phe Thr Ser Leu Arg Asn Gly Gly His Leu
                530                 535                 540

His Ile Lys Ile Lys Leu Ser Gly Glu Ile Thr Ile Asn Thr Asp Asp
545                 550                 555                 560
```

```
Ile Asp Leu Ala Gly Asp Ile Ile Gln Ser Met Ala Ser Phe Phe Ala
                565                 570                 575

Ile Glu Asp Leu Gln Val Glu Ala Asp Phe Pro Val Tyr Phe Glu Glu
            580                 585                 590

Leu Arg Lys Val Leu Val Lys Val Asp Glu Tyr His Ser Val His Gln
        595                 600                 605

Lys Leu Ser Ala Asp Met Ala Asp His Ser Asn Leu Ile Arg Ser Leu
    610                 615                 620

Leu Val Gly Ala Glu Asp Ala Arg Leu Met Arg Asp Met Lys Thr Met
625                 630                 635                 640

Lys Ser Arg Tyr Met Glu Leu Tyr Asp Leu Asn Arg Asp Leu Leu Asn
                645                 650                 655

Gly Tyr Lys Ile Arg Cys Asn Asn His Thr Glu Leu Leu Gly Asn Leu
            660                 665                 670

Lys Ala Val Asn Gln Ala Ile Gln Arg Ala Gly Arg Leu Arg Val Gly
        675                 680                 685

Lys Pro Lys Asn Gln Val Ile Thr Ala Cys Arg Asp Ala Ile Arg Ser
    690                 695                 700

Asn Asn Ile Asn Thr Leu Phe Lys Ile Met Arg Val Gly Thr Ala Ser
705                 710                 715                 720

Ser

<210> SEQ ID NO 3
<211> LENGTH: 45839
<212> TYPE: DNA
<213> ORGANISM: Homo sapiens

<400> SEQUENCE: 3
gacttgagtc tctaagggat cgcaaattgt aggaaggcaa atatacaaga aactaatggt      60
aggtaaaggc tggttagtaa aatttgttag gaagattcct ctggtctaaa aggccctgaa     120
gacatcttca ttgatcaacc tttgtccttc ccagtagaaa gggaggagg acacctatgt      180 cctgctttag gcaaatagag gcaaacagca agcttttctt atatctgctt cttctcaact     240
gctttcagct taaaataatc ctcatgtcaa atggtatatt tggtgtggaa gagcctgcta     300
cctttcaaca gaaccagagt ttaatgaagg gacgatttac agaggtgtgg gcaggattag     360
ggacatccag gagagatgat ggggcaccta gagacaagca cagtggaaac tgtcgttgtc     420
cctagccctg aaggaaggag agagacaggt ggcattacag ggcccaggga agttggagt      480 agaggttgag gaattgccca acagaagcag tggtggtagg tagaggaata taaccactgc     540
caaaattata cccagcagcg ggaaaggaat caattttctg acctttctcc cctcccatca     600
tctgactaca cgggccatga aatctgccaa ggttggcctt ctcagcatag accaggacag     660
aggagagaga ggacggatct ggagaggtga atggagaata acaaaataca atttcaaaaa     720
ctctacagtg ggggagcttt agaaacagtt ctattatctg tacaggacac attctatttt     780 ttttttttt tcgagatgga gtctcgcttt gtctcccagg ctggagtgca gtggcatgac     840
ctcggctcac tgcaacctcc acctcccggg ttcaagcgat tctcctacct cagcctcctg     900
agtagctggg attacaggca cgtgctgcca cacccagcta attttgtag ttttagtgga      960 gaccggcttt caccatgttg gccaggctgg tcttgaactc ctgacctcgt gatccacctg    1020
cctcggcctc ccaaagtgct gggattacag gtgtgagcca ctgagcctgg cctgtacagg    1080
acacattcta gatgtgcagt gattccattt taatgtaagt gcttctcact tagtctcatt    1140
ttcagcaact ctttccaaga ttatttacag gcttgatcta catgaatcta ggaaacaccg    1200
```

```
tggaccctgg cttcacctgg gggtggagca agggcctgag aggagggctg cacgatgctt    1260
tgagtgatag gggatcctgg acactgggat gtgtggcctc tccagggatt ttcgagccca    1320
tgaaaatgtc agaaaatccc ccataacaag aggccactgg gagcttggcc aagggtgtcg    1380
tgtggttgga tatctcaagg ttgcttgtgg caaacatgaa actggaggtc tgagaccctc    1440
tgccccttt ctggcaccac tagatatcca gggttctgat gggtctctga ggtgggggt      1500
gggaggtaac taacactgat ttcagtggct tttcctacca cttccatggg atatgtgtgt    1560
gtggggatg gaatttgggc ttgaattcgt ttctgatcca taaattgggg ataataatat     1620
tacctccttc acatgattat tgggaagatt gagatgatca tatacgtaaa gaatttagca    1680
gtctggcacg taggaagtgc tcaacatatg ttagctatta gtagcagtcg tagcttttcc    1740
ttctgtctac tgaccggaag gtgctgtttc tgttttcat atgacacatt gcaaagtgac     1800
tttgaacgta tgattcttaa tttcatttct tgcaagtgtg aaatgagctg acagaagaga    1860
ccaacatgga gagcctcacc cccacggccc acagcagaca catcacagag ttaccaggaa    1920
ttccagaaag gaagtcaagt gatgaaagac tgaaggatgg gaaccctggg aggactgctc    1980
cctaagggaa gctgggtgga aagttctcac ggagtccagc cccgttccgc ctgctctgcc    2040
ctgggggtct cccagcccct gtccctccgc gaattgagga gcggtcctaa ttgccagttg    2100
ccttaaagag tttggggaaa ctgaagactg ggtcccttta taggcaggtt ctggatcaag    2160
agggggtgggg agaggccctg catttggatt cctgaaatcc acagaaaacc ctgcccttac   2220
actactttat tttaaaggtt ttgttttttt ttaaattaca aaagtaaaac aagcgtgctg    2280
taaaaatagc ataaacatgt acagtgcata ggctgggctc ggtggctcat gtctgtaatc    2340
tcagcacttt gggaggccga ggaaagtgga tcacgaggtc aggagttcaa gaccaacctg    2400
gccaagatgg tgaaaccctg tctctactaa aaatacaaaa attagccggg catggtggca    2460
gtcacctgta atcccagata ctcgggaggc tgaggcagga gaatcgcttg aacccggggg    2520
tggaggttgc agtgagccaa gatcgtgcca ctgcactgca ctccagcctg ggcgacagaa    2580
tgatactcca tctcaggaaa caaacaaaca aacaaacaaa caaacaaaaa ccatatacag    2640
tgcataaaga aaaaggcaga agtccttctc caggtggcct ccctgcccaa atctgctcct    2700
cagggtgggc cctgaggctg ctggagtctc ctgtgctggg gagccctcca cgctgcctcc    2760
ctccaggcct ttaatccagt cttgaggtgc ccgaatctct gttttgtaca cctgcacacc    2820
ttctagtggg ggtactttgc aaactcaatg tgaggacaag cagatggaat ggcaagtggc    2880
aggtgtggcc taaggtatcc tcccatcggg ctcccccacc cttggaaatt aggatcttaa    2940
attttggtcc tgaccaagtc ccactaaaac ttggctacta ggttggtttt ccaattccag    3000
ggccaaaagg aaactgggaa caatgatacc tactagcaaa agaaaaaaaa ccaaatttgt    3060
tagaacagtg accctaacta gtcaaaggca gtgctttcac ctagaggtaa taataataac    3120
cacttctggg agcccttatt gaaggctggg ctttgcttta agagtgagga ctgctaatat    3180
ttctcttttc tagatgagga cactggtgct cagggagatt cactgcagga ggcaggagag    3240
tgcagtggtg aggagctcag gctctgcggc ccgaccacct ggtcatccat cctggttctg    3300
ctgcttatca gctgtgtgac ctcagactta cattatggag tctctcatga cttggtttcc    3360
tctctagtaa aatggggatg atgacagtgt ctccctccaa gggggggtggt gattaaatga    3420
gttactatgt ggctgggcat tgtggctcat gcctgtaatt gcagcacttt gggaggctgc    3480
agcaggagga tcacttgagc caggagtttg aggttacagg gagctataat cgcaccactg    3540
tgttccagcc tgggtgacag agtgagacct tgtctcaaaa aaaaaaaaaa agagtatgtg    3600
```

```
tcaagtgcct ggcacagaga agatgctcaa taaatatgag aactgggatt aaattatggg    3660
cctaagtctc agctagtggc tgatggagaa ggcatctgaa tccaggtctg atgtggttga    3720
gggtcaaggg cttacccgct atgtagtgct gtctccctag agcctgccgg ctctcaactc    3780
ctctcccacc ttcaaggcct agatcctcgg gagtcccagc tgtcactgat gtgaggatga    3840
cacgtgtctc ctctgaagaa ccaatgattc ctggtgagtc atgggaggca gagaagactc    3900
ttggactttt ggcagaagat ggttagccct gggcctttct cctcggagga aagcctgtaa    3960
gtcccttgcc ctgatgggtg cttggcaggg aggatggggg attccctatc tttctaggga    4020
tacccctaaac tcaagtaccc tcattatgat acaggatctg acgcaagcat aggggaagtg    4080
tggctgcctc ctaagggtgg aaatagcaat gaaggaggct gtcaaacatg atttgctgga    4140
gtggtgatgt ccaacctgag tcttcaaaga tgggggaag ttatgaaggg aggggaagga    4200
cattctgggc agagggcaca atttgagcag agaggctaga catggtatct gagaaggatc    4260
aagtctgaag aaagaagcag caaaagatga ggctgcagag gtcaacagtg gtcagaattt    4320
ggaaatcttt gtataatctg ctgaaatgct tggactttt ttgatcgaaa atagggagcc    4380
aatgaagagt tacagaggag ataacaatgg taaagttttg tcaggtgtaa atgggataa    4440
ccatacagta accctacaat cataggattg taggattatt gtttggttat cccattttac    4500
aatcctgcat aggattgtag gattattgta taatcataca ttattataca ttatatatta    4560
taatcataca ataatcctat gtaggattgt agaattattg tatgattaag tgagatgatg    4620
catataaagt tcttagaatg gcacctaaaa aatgctcagt aaatgttaat gatgttgatg    4680
ctgatgactg taatgtccta ttaggaagag aaaccgcaaa gttagaggcc acctaggcag    4740
tccatacagt aagtaaggcg tggccgggtg gatgaaggcc aagaccagcc ttacatagaa    4800
atccagtcca tgccagtcca tggacttgac tgcctgctgg agtaaaaccc aagctccttg    4860
gcgtggctca aaagcactag gtgacctggc cccttctcac acgttaggct ccagccacat    4920
tatttttcttt ctggtcttca agcatgtcca aacttgtcct gtgtccttgc tgttccctct    4980
gtctagactg tccatccctc acatctttga atggctgcca cttctttgtc acaaagctct    5040
tggttcaaat gttacttcct ctaagagaac ttcttgagcc ctagaacatc agccttctcg    5100
ccaaatgaaa tgatcttact tgttttcatg tttagtgtct attgcttcct atcccctaga    5160
ggatgtaaac tccataagtg tatgaattat atctttcttg ttcactgctg tatccctagg    5220
tccttcaaca ccgtctagaa catggatacc ctcaataaat gttttccagg aaaaaataaa    5280
ggatctgaaa tgatgtctat tagagtcatt cctttcaagc tattcctggg agaggtagct    5340
gatcaagctg tgatcagcta gtaacacagc tgagtgaatt cagtgagatg atgactttgt    5400
gtaggtagaa tctggggact aaagagaagg gacatcacaa aacgaagtaa gttccaatga    5460
cccagggtaa tttccatggc accgctggtc agggagctgc tataggactt gggtgtagac    5520
aggtgacaga agggtggggg tggagacagg atagaaagag gctgggtctt agaagcatgg    5580
tccatcagag ggggcctgga gggccactga ctcaggtctt acattccatc gagatcttta    5640
aatttaggct gggagtagtg gcttacacct ataatcctag cactttggga ggccgaggct    5700
ggaggatcac ttgaggcaag agttcgagat tacagtgagc tgtgatggca ccactgcact    5760
ccagcttggg tgacagcatg agacctcgtc tctaaataaa ataaaataaa atcaacttt    5820
taaaaagtaa caactttcaa acttagtctt ttaacattat ttagtatttt gatattatct    5880
ccaaaagagg ttcaaatag tcacagacac accaacaggg ttgaaaaaaa tgctcatttg    5940
tataactgta attacaaaat gcaagtatca agaatattcc agaactcatc tttctttttt    6000
```

```
ttctttgaga tggagtctcg ctctgtcacc caggctcgag tgcagtggca agatctcagc    6060
tcactgcaac ctccgcctcc tggttcaagc gattctcctg cctcagcctc ccgagtagct    6120
gggactacag gtgcccacca ccacacccag taaattttg tattttagt agagacaggg      6180
ttgcatcatg ttggccgggc tggtctcgaa ctcttgacct caagtgatcc gctcgcctcg    6240
gcctcccaaa gtgctgggat tacaggggtg aaccaccgcc cctggcccag aactcatctt    6300
tcaaaactgg cccgcagcat ctgacacagt tgttttcctc cttctggcca ccctctcttc    6360
gagcttccag gacactatac tctcctgatt gtacttcctt gctggctact ccaagtctcc    6420
actagtggtc cttgctcatc tcatcatcca ccccagattg tccatttcca gaaggcagca    6480
gagtgagccc cgggggcctc acctgaagtt cctctgcagg aacagcctcc ctcgaggctg    6540
gcttcctcac ttcctaatag tcctaggctg aaggtcactt tctcagagag gtctcttcc     6600
taccaccta cttaacactg cattccctcc aatcctctct ccctcttcc ttcccttaat      6660
tttctctagt gctcactacc aaatgacatg cattcttgt ttagtgcttg tctcccctga     6720
ctagtatgtc agttccagga aagcagaggt ttgtcttttg tttactacta tttattatct   6780
agcacagtgt ctgacacaca ataggccctc aaggaaattc tgttggtcac ttttcaattt   6840
tgctggtttg cacttaaaaa tatataggga gccttaccag gagccctaga ccgaacgtga   6900
gtctaaggat tggtatggtt ttcctccata caacggctaa agcaagggac agagccgaca   6960
ctcaaggaat atttcttgaa ttaatgacct tctggagtgg ggtagcattg tgtcaagttt   7020
gcagggtgca gcttggatgt ggtgctagaa gggaagcct ctgggctgag catgtaggct    7080
cgtcagtaga gttcaacccg caggagtaaa ttactgcagt gggaaacaac cgcacccgcg   7140
gcccagcagg ggttccactg cgcagccgca aaaggcgccg aggctccacc gcgcagccac   7200
agaaggcgcc gaggctccac cgcgcagccg caaaaagagc ggacgggtct cgccgccgc    7260
aggaggagca ggcggtacct ggacgggttc gtcccgggct gtttcgcgtc cggcctgagg   7320
cggctgggc cgcgcaggta gtgtccctgc acttcttgcc cgggcgcgtg aggccagctc    7380
cgctgcgctt gtctccagct tccagccctc ctccctaag ccgccgccat catgctgctg   7440
cctgtgttca ccctgaaact gcgccacaaa atcagccccc gaatggtggc cataggcgc   7500
tacgacggga ctcacccgtg cctggcggcc gccacccaaa cgggcaaggt aaccgctccc  7560
accgcaggg agcccgggcc ccagggaacc acaggatctc gccggccgc gccctggga   7620
tcccgtcccc ctccgaccc cgccccagc ccgtgttgcc cggcaaccgg tcggcgagca     7680
ccttgtggct ccatcctgca gaggacagtg gggtcttaga ggaagagctt ttctgagaag   7740
ttgacgtttt cttgtcatca ggcacttgga gtcaggcgag gtcggggtcc ctggacatag   7800
ggagcttaga aaagagacgt ctcctgaggg aaggggtttg gttcgggtta gcagtaataa   7860
ccgaccccag attcaagcca ggggcctctg cttgtcactt ggaactcgga attcctctga   7920
ctctctaaca ctgcttcttc ttcctttttt tttttttt tttgagacgg agtcttgccc     7980
tgtcgcccag gctggagtgc agtggcgcaa tctcgggtcg ctgcagcctc gcctcccgg    8040
gttcctgcaa ttctcctgcc tcagcctccc gagtatctga gattacaggc gccgccacc    8100
acgcctggct aattttttgta tttttagtag agacaggatt tcaccatgtt ggccaggctg  8160
gtctcgaact cctgacctca gtgatttac ctgcctcggc ctcccaaagt actaggatta    8220
caggcgtgag ccactgcacc cagccttca cagtccttta ccgaacaacg acaaaagaat    8280
gcaatacaaa aattaactta ttcaaattgc acttttgatc cttgcccatg tacattcagt   8340
tcttccccg taatttattc actaagtatt aggtgtttac tatgtgcgat tactgggcaa    8400
```

```
gatgtgagag tcaaagagat aaaagagaaa tcatgtaaca ttcaccagac ttctactaaa    8460
caccttctgt atagattttg gagactcgga tgtaaaagga gtccctactt tcagaaagct    8520
tatagtccag aagctaacag acaaggcaaa tcagagccct gtgtatttga cggaggcatg    8580
cccaaaatac atggaatgta gtgacaacgc taataactta taacaggcac aaaactttat    8640
tacatgagtc atctcagcgt cgttgtcaca aggccaacgg cagcagcatg gcatagggat    8700
ggtgtttctt ggctccagta cctactaatt tcatgacctt gggcaaggca cttaataata    8760
gtacctaata cgtggggtca tgagctttaa aaaagttaat acatgtaaag tgcttgacat    8820
ataggaagtg gtcactgatt gttacctgtt attttctttt tatggttctc actttattga    8880
ctagaaattg cagttcagag aggttcaata cagtgcttgg agccactcaa ctagaaagtg    8940
tggaatgtgg tcagagtgca tgttctctga tccagtgtgg atttaataag ctaggatttg    9000
tgtaacaatt tatagttttt aggacacttc catgtatatt gtatgttata tgccttggga    9060
tacagaagta aaaataagg cttcattttc attaagtagt ataacagagt taagctatta    9120
atacggggtc tggcacatca tgatgttagt tattgttaca gttagaagtc actgacaggc    9180
tgggtgcagt gactcatgcc tgtaatccca gcactttgag aggctgaggc aggcagatca    9240
tctgaggtca ggagttcaag accaacctgg ccagcatggt gaaaccctgt ctctactaaa    9300
aatacaaaaa ttagccaggt gtggtaggtg cctataatac tagctactcg ggaggttgag    9360
gcaggagaat cacctgaacc taggaggtgg aggttgcagg gagccgagac cgtgccattg    9420
cactccagcc tgggcgacag agtgagactc ggtctcaaaa aaaaaaaaaa aagcactgac    9480
aaatgccaaa aagaacttca tgttgcttgt gctgtaggtg catagcagat ttataaatgg    9540
gctgaaaata tcccattggt attaactcag cccctaattt gagggcttac tatgtgctgg    9600
gcagtcttct tagctctgca ggtgcattgg agaatgtgac agacaagttt ttgccccctt    9660
ggagcttaca tttgagaggg ggaaccaggt agttaactga atatgcaagt gttttcatag    9720
gagaaaaaga ataagggatt cagtgtgatg ggagcttggt gtcttagaca ggtggtcaga    9780
tggcctctaa taacatttga taagaggttt gaaggaactg aggaaacaag ctctgcagat    9840
ttgtgggata agcgccttgc aggcagaggg atctgcaggt gcaagggcct tgagctggag    9900
atatgcatgg tgtgtttcag gagcacaagg aagccgctgg ggctggaagg caatgagggt    9960
ggtcatgagg tagacacaag ccagatcata taggaacttg taggccatgg caaagacctt   10020 ggttttata ctgagtaagt taggaagtcc ctgaggattt tgataaagtg ggtgttggaa    10080
tttgctttat gttttagata aaggctaact ggctggtatg tggagaacag atgttctgtg   10140
acgggatgta gggaggtagg tgtcggagta gaagcaggga gatcgggcag aggtccctag   10200
ggcagcccct agatagagtg tgacctggag tggaaggcag gaatgcttga ttgtagggct   10260
gttgtcgaaa atggcctaat aataataata ataataataa ataaaataaa ggagatccct   10320
tgtcctgtgt aactggatgg atactttgtg ttcagctctg taaacaaatc taaaagttc    10380 tgacctgatc ttttatcttg agaccttaaa aagaattagt agtatttat gactcaagta     10440 atgccatgaa tatattttct taaaagcaat taaaacattc cagctagggt taaagcctgc   10500
atgtctagaa acaggacttt atccttacag ctgggaccct gttgtgaaca tggagctgac   10560
tctgagcctt agcaaggata ttttttttaaa aggaatctct ggccgggcat ggtggctcaa   10620
cacctgcaat cccagtactt tgggaggctg agaggggcag atcaactgag gttaggagtt   10680
cgacaccaac ctggccgact gaaacccgtg tctactaaa aatacaaaaa ttagctgggc    10740
gtagtggcgc accctgtaa tcccagctac tcgggaggct gaggcaggag aatccctagg    10800
```

```
acccaggagg cagaggttgc agtgagctga gattgcacca ctgtactcca gcctgggcaa    10860
tagagcaaga ctccgtctca aaaaacatat aaataaataa aaggaatctc ttgcagggtg    10920
aatattagag ttttcctctg gggacatttt ttctctcatg gtaatgctta ggggtcagtt    10980
gaatttatat tgtttgcagc acctcctcag ctagaacaaa agtgtgaact tcagcaagtc    11040
ctttgaaagc cctgggagtg gtcttttttgt cgtatgactg agattggctt tctttccttg    11100
cctgaaggga cagacttgtc tccctgtgga ctctctttga gtgtagagaa cagcaggagg    11160
gaactggggg aaagtctgac tcctgagatc cttgttgctc ttgacaaaaa ttgcaaactc    11220
tttccattcc ggtaagaatg aatatggagc ccgtaagcta tttctgctcc tgtactttct    11280
cagcatattg gatttctgga aaactttgta agaattggtt tgttcagaac tgttataaaa    11340
ggaagtgtga tgtggtggtg gctggagcgc agggcctgga gcacaccagg ctcttgtctt    11400
agccctgtca ccagtctcaa gaccttggca aagggcctta actcttccga cctcatatgg    11460
aaatgaaggg ttggtgtcag gttcaaatgc aattaacatt gaccaaggca tgttataaag    11520
tgttacacaa acggaacatg aaggcagtgt tcagtggctg cacgttttct atgtttttag    11580
tcaattcttt tgaaaattat ttttgttga ataggctgcc ttgggtaggt gttaatttaa    11640
aattaattct gtttggattt atgtgaaaga gatgaaatac tcatgtaaat tttaaaaatt    11700
ttagaactag aaggggctag agggatccct agtccagtgt ttttcatcct cccaaccttt    11760
ttggtcatat tgcccacctt ggaacttttt tagaccaaga aaattttccc agtgaaattc    11820
tgatacctca gatatacttt gtatctcttt ttgtactgtg gtcctgcgaa gggctacacg    11880
attccccatc gcaaacccat ttacctgtcc tgggagtgat ctcgcccctc ttaagactgc    11940
attttatagt ccaaacctcc ttttttacagg tgaagtctag gaaagttgaa taatttatgc    12000
agacactcag attatattta tgatagttga aactgttgaa tttattatct ttgggctaat    12060
tacttagttc tatgtcactg gtataaactg tgaaagcctt caagatactt gatttgcatg    12120
actcggttta agtttgtgaa acaggtttac taactagcag accatttaa ggtctaggaa    12180 gtgattcatt aggtgcttgg atgaaagata ataaggaag tgtttattct gttttccatg    12240
atcttcttgg tgtgtggcaa tcacattgaa ggtggtagca gcttattcta ggttgatcgg    12300
gaaaaggcta gctcctaaga gtgctttgac atcctgctgg tgggtagcat gtaagctggc    12360
ctggtaagca gtgactagat cttgttcatt accttgttcc ttacaaggct aagaaccact    12420
ggatttccgt gatttcataa tgactgaaag ttgtccatgc attgaactat gtacgagtgt    12480
tttaagtttc ataggagatt aaagtgacct cttgttaatg tggatgtgtt aataacctgg    12540
ttctttttta aaaaaatgta tgatactaat ttttatatt ttaagggaat gtaattagtt    12600 attttgttt caggttttta ttcataatcc tcatacacgg aaccagcatg tcagtgcatc    12660
cagggtcttc cagagccccc tggaatctga tgtttctctt ctcagcatta accaggcagt    12720
cagctgtctg actgcaggcg tattgaaccc tgagcttggc tatgatgccc tttagtggg    12780 gacacagact aatcttttgg cttatgatgt ctacaataat tcggatttgt tctacagaga    12840
ggcaagtata acctttataa ccataaaatt gtcattactc attaatgtcc atttttatg    12900 cttagaagag atcagatcat ttattttggt ctgtttgttg tatgactgtt atagtatagg    12960
taaacaacat ggagattttg ctgttaacat ctgcttatg tactcggaac ttatttattt    13020
ggttatggtt gctaatcgct tggtgacact cgagcttatc tctatgaggt atatctgtga    13080
tactgccatc tgtcaagatc tgttgagaat tcagccaaga gctgggaagc caatagacag    13140
gtctcctggt ggacttgcat tcaagtttag tgcaatagtt tgtagaagcc cttactgtag    13200
```

```
cctgccacct acaggctgct gcaactttaa tacccaagca attcatattt gttacagaaa   13260
agataaggaa gtaaaagta aaagaaatta cacctatttt ttcatctaga aagagcactt   13320
aactgttgag tttttgaatc cagatttttt accaagcata tatgaataca ttttgtagta   13380
aaatggggtc atatatacat gtagccttt acttgtttt acccctatagc agctttatta   13440
agatatgatt cacatgtaca actaacctac ttaaagtata caattcagtg ttttttagtg   13500
tatccagaga gctgtacaac catcaccatc atcaattttc aacatttta ttaccccta    13560
aaaaacccat acccattagt atcactcccc attttttcttt aacctcctaa ccttaggcaa   13620
ccagttatct actttctgtc tctagaagtt tgcatattct agacatttca taaacaatgg   13680
aattatataa tatgtaatca tttgtgactg ccttctttt cttagcatga tattttcaag   13740
gttgatccat gttgtagcat gtgtcagtaa ttcacttta tggctgaata atattccatt   13800
gtatgtatat accacatttt atttatccat ttatcagtta atggacattc cactccctgg   13860
ctattatgtg tggctctttc attcaataat atgttgtgaa catctttata tgaagttact   13920
acatacccgt tatgtcattc ttattggttc tgtagtattt cattgtgtta atgtaatttg   13980
tttaaccgtt ccatgttgtt gaacattat gttatttcca ttgtttctgt attacagttc   14040
atagtgtaat aactgtatct ctttgaccac ttccctgatt atttcctgag gataagttcc   14100
tgaaaatgca gatggttttc tttcttttg ttttgtttt ctgagacaga gtcttgctct   14160
gtcacccagg ctggagtgca gtggcatgat catggcttac tgcagccttg acctcatggg   14220
ctcaagcaat tctcccacct cagccttctg agtagctggg actacaggtg tgtactacca   14280
cacccagcta attgttttatt ttagagag ataggtctc actatgttgg ccaggctggt   14340
ctcaaactcc tgggctaaag cagtcttcct gcctcagctt cccaaagtgt tgtaattata   14400
gatgtgagcc actgcatttg gctggttttc ttcttgtct atttttgtt gaggtaaaat   14460
gtacatacat gaaaatgcac agaccttctg tgtacagttc aatgagtttg gatccctata   14520
accaataccc caataaaaat agagaacatt ttcatcacct cagaaaatat tgttgtaccc   14580
cattccagtc aatttctatc tcccatagac aatcactgtt ctgacttctg tcagcttaga   14640
ttagcttttc ctgttgttga actccataca aatagtgtct ggcttctttc acttaacata   14700
atacttgtaa gaattatcca tattgttgca tataaaagta gtcttttgtt gttgttgcta   14760
agcaacaaaa atagtatatt ccattgtgtg aatatactat ggtttgttta tccactctct   14820
tggtgataga caagtggctg gacatttgga ttgtttcagt ttttaacaac catttttgtt   14880
taagacttgt ttttaataag actttttat ataagacttt ttgtagatat atgtttaat   14940
ttatcttggg taaataccca agagtggaat tgctgggcta tgtggtttat aagaacttta   15000
tgacactgtg aaactgtttt tgcaaagtgg ttgtatcact ttatactcct gcctgcagtg   15060
taggagagtt ccagttgctc cacatccttt gtcaacattt gttgttgcca gtctttaatt   15120
ttagccattt tggaaggtgt gaagtgatat cttaggtgtg gtttcatttt gcattccct   15180
gataatcatt gatgcagagc acctttctt gtgcataaat ggacatttat gtgtcttccg   15240
tgaagtgtct taagtctttt gcctattttt tattggtagt ttgtctcttt attattgatt   15300
tgtagacatt tcttggatat actggataca aactctttgt cagatttata tataataaat   15360
attttctccc agcctgtggc ttgttccact aggcatgtgt cttttgatga gcaaaagttt   15420
tgcatttttg tgaagtccag ctgatcacat ttttctttta gtggttagga cttttctgc    15480
cctttgccta tttcaaggtc acatcgtttt tgttcagaag tgaaatcgag tttaggactg   15540
tattagtcag ggttctccag agaaacagaa ccaataggac atgtacatat tagaggggga   15600
```

```
aatatttatt ttcaggaatt ggcttatgca gttgtggagc ctggcaagtc aaaaatctgc   15660
atggtgggcc agcaggctgg agatctagga gagaattgat gttgaagctc aagtacaaag   15720
gctgtctgct ggtagaatcc cttcttcctt gggggaggtc agtctttttt ctattaagtc   15780
cttcaatact tgatagaaag ttcttaatag aaagtattga aggacttaat agtaaagtag   15840
attattatcc atatgtgcgt gggccagtta atgtgtgagg cccacccaca ttatggataa   15900
taatctgttt tactcaaaat ctgctcagtt tactcaaaat ttggcccaat taatatgtgg   15960
gcctgcatat tatcgtgtct aagataatgt gtccttttac ttttcttagg tagcagatgg   16020
ggcaaatgca attgtgctgg ggacattggg agacatttct tcccctcttg cgattattgg   16080
tggcaattgt gctctgcaag gtttcaatca tgaaggaagt gatctctttt ggacggtatg   16140
aagaagaaaa cattctttt ggtaccctta agcattttta cttttaatgt tctttttaa   16200 ccaccaactc tactgagtaa taatatttat aattctgtgc attaaaaaag gatatgaata   16260
attcgaatag cattcattcg tgttttgtgt aatcctctcc ttcatgtagc taatatattt   16320
ggagtaaatg gagaaacgat ggcatgctaa tggtttgggg ttttattttc aggttactgg   16380
agacaatgtt aattccttgg ccttgtgtga ctttgatggt gatggaaaga agaggtatg   16440 tgggggagga gatatctctc ttgtgtgttc agccaaatga attttgccat gacagtgaca   16500
ttagtgttga cagaagtgta agcttctcct ggctgatttt ggtgctctgt tgcctaaatg   16560
ctcagccagt tggccccatt cgtctttctc ttctcttttg aacaataaat cacttgtgct   16620
tgtgtaataa atacaaagat caaagccatg gtgtttcaga gacacaggag agggcagaga   16680
gggtagaaga gttgggattt cagtcatatt cacggtctta tgaattgctc ctgatgcttt   16740
gaaaccatat tagtatatag ttttcaattt tggccaactg ttttgaggaa tctaaatgtt   16800
ttagagattg gcttttagcc tttgaaatta ttcttatggt taccctagaa attagcttct   16860
tgagcagtta gtaggtgtga cgtgctgtgt tgggcaccga cttgcccctc tcttgtccat   16920
ggacactgga ctctggtgtt tgaacagggc ttccatctgt aggcagagaa agttgctgat   16980
ccagggagcc ttttcaggta ctcagggaaa taacgtattc tggcaagatg tgcagctccc   17040
atggcaggat aaaagctgca gtagcccctg ttccttcatt gattgaatct gctgatcctc   17100
ccattagagg gagcatttct gagcatcaaa cgattatgag gttgtcaatc ttgggtggca   17160
gaagcagcat gcaaagtact gtgcaatttt ttgttttgtt tacagaaatt ttgttgtttg   17220
cacttactca cctgaacatg tatgatattt ccccttcagc ttcttgttgg atctgaggat   17280
tttgatatcc gagttttta ggaagatgag attgtgcag aaatgacaga aacagaggta   17340
agaagctcca cctcgaacta tggtaacctt gagcaagata gatcagtact gtcagatgaa   17400
acatcaagtg agagtgctgg ggcatctcca aacccaggtg gttttaggat aaaagcttgg   17460
ggagggggtc agacagagct gtatgttatg gtaagaaaag caataaaaat cctaattaag   17520
atatattttg aaaagactga ttaaatagag aaaaattatt gcatatagtt gaatacataa   17580
aggcatttct tttaatgagt taatacatgc aaataataat aatggcaatc atttattatg   17640
tacctattgt atgccaggta gtgctctaag tactttatat gaagtaacat attgaatcct   17700
tacaacaacc ctaataggaa gataaattat tattatttct atagatgagg aaaatggtgt   17760
tctggttttt tgtttgtttg tttgtttgtt ttgaggcaga gttttactcc atcacccagg   17820
ctggagtgcg gtggtgcgat ctcggcttac tgcaagctcc acctcccaag ttcaagtgat   17880
tcgcatgcct cagcctcctg agtagctggg actacaggca cgcaccacca cgcctgggta   17940
atttttgtgt ttttaataga gacggggttt caccatgttg gccaggctgg tgttgaactc   18000
```

```
cagacctcaa gtgatccgcc caccttggcc tcccaaagtg ttgggattac aggggtgacc   18060
caccgcgcct gtattttttg ttaagttact tgtacgtagt cttggctatg aaatggcatg   18120
gtcagcattt gaacctttat gccccttcct cctcatcatg tgtattcagt agggctgaag   18180
tgcataaatg agatgtctat attttttttct tcctgcaaat tcagtacttc tttggcacat   18240
ttctgtaggt aaacttaaaa attatagaac ttgtgattag aatcactcat gtaactgaac   18300
ctgagatatt tcttaatatc ccaggttgtt taggcctgat gtttaggcct ggtgcagtgg   18360
ctcatgcctg taatcccagt gctttgggag gccaaggtgg gaggatcact tgaggccagg   18420
agtttgagac cgcctgggc aacataacaa gactccatct ctacaaaaaa tattaaaaaa    18480
ttagccagaa ggtgatggca cacgtctgta gtcccagctg cttgggagac tgaggcagga   18540
ggatcccttg agcccaggag cttgaggcta cagtgagcta tgatcacgcc actgcattcc   18600
acccaggggc aacgagaaca agactctgtc tcaaaaataa aattttttaag aagtaacagt  18660 gttaagagtt aggaaaataa agacaaaaat aaagcaaaaa gcactatcta aagattacct   18720
gtatccttta tggttttgac attcttagga tatttatttg ctgctggttt tccaggattg   18780
ggcaagactc aaacagaaaa aaataagata ttcttaatta aggaataaga ggataaagga   18840
gcaatagctt gtgaacgttg taagtggaca gaaagaaacc agtaaaagag agtcttagag   18900
atcagaatgg tgggatttttg caaaatttag ttatgtggta tttaggagtc tgtatcagaa  18960
aagctcgagg gcactagtct caaaactgac cttggccact tgtctttaaa ttacttgctt   19020
catgtcactc ataaaagctg cctaagaagg tcagacttct tttctcctaa ctataaaagg   19080
agacaaaaag caaaacctac acattgacat acagtgctac caatgatttt aactaagtta   19140
tcctatagca agagtcatca gttttttattt agtcctacta tacttttttat atattcacag 19200 ttatcatgat gtaagatgat agttgtggac agagaagaaa tgaagaggag aaatgggtgc   19260
caaaaggagc agtctgagga tgtgtgttta tacagggagt ctgtttttta ttttattatt   19320
tttttgagat ggagtttcgc tcttgtcgcc catgctggag tgcagtggcg tgatcttggc   19380
tcactgcaac ctccgcctcc caggttcaag tgattctcct gcctcagcct cccgagtagc   19440
tgggattaca ggcacctgcc accgcgccca gctaatttttt gtattttttag tagagatggg 19500 gtttcgtcat gttggccaga ctggtcttga actcctgacc tcaggtgatc cacccgcctc   19560
agcctcccaa agtgttggga ttacaggcat gagccaccat gcctggcccg ggagtctgtt   19620
ttgtgtgtat gtgcttatat gtgctttctg aagagagggc ccggagcctt cattacattc   19680 ttaaagggt ttgcaacctc ccccaccacc aaaaaaaaac aacttgagaa tccctggctg    19740
atagatggtg tgtcccgaat tctcatatcc ctttcattct aatttgtggt aaatcttttc   19800
tcctttggtg ggaatcattc agattttgtt ggatttttat tgcttgttaa tattagattt   19860
gaggagactg aattctttga aacatctctt tcctaaatcc tagaaagag gacaagaacc    19920 tggaatagag ttagggattt gagggactt gttgatcttc tagtccacaa aaggaagaaa    19980
ctggtgaact aaggaagcag taaaagagct gaggaatctg gggctaaatt tatgaaaata   20040
tggacttcat aacattgttc acttgcaggg ccatttttcct gttctctttg ttaggttttg   20100
ctcctagctc aaatatcatt tcccagatca gcaaaatcat gattcatttg gcagttgaac   20160
agtatgaagt attgtcagaa gaatgccttg agctaaataa ttctggaatc ctacacagca   20220
ctttgtattc atagttaagt gaagtgggtg gttttgtaga aaagctgtag gtgtaaagga   20280
aattatataa ctattctctg ctttatacaa tttattttctt aatatctctt gtattaggaa  20340
cagaattaga aagtagatct gcaggatcat ggatatcatt aagctttggt tttaacttta   20400
```

```
aaggaaagtt ttgttcagta cctaaaattt tatccttta aggatgtcaa atccttgaac   20460
agtcctataa atatttctgt atcatatatg cattctgtat attgttatat actacacaaa   20520
tccacgtgcc tgggttttta cttttcaaag gattatgtgt tctttctttt acctctagca   20580
aacaaattat gtcatagaaa gaaaagtgta tacatgaagt aagatattca attgtgtatt   20640
gttataagtc ttttaaaaat tgagactgta ggatgttata agttaagtaa taatcattaa   20700
agcctcttgg gtgaacatat ataatatcta ttgtatatgc atattttcga tcttgtgtag   20760
ttagcttatg ttttccttag tccttcagtt ttcatgtgtt ttttaaaaat aattttgtga   20820
aacttgccac ataaggttgc tctaaaacac caaaccctgt gagtttattt aaatctgatt   20880
atacaactct gaagtagatg acatgtatcg tagagaagag gaatacattc cccactaatg   20940
gattggaagc gcttttaaat ctaattttaa catagttgta acaaggagtg tgaagtctta   21000
taaagccgta cttgacagta aactgagtct taatgaaaag atgttgtgtt tttgtggatt   21060
gttttgcaga tagtcacctc tctttgtccc atgtatggca gtcgatttgg ttatgccctt   21120
tccaatggca cagttggagt ttatgacaaa acatcccgat actggagaat taaagttagt   21180
ataatttagc ctttgatatt caggcgcttg atagttattg tgagacttct gtgctaatta   21240
ttaaaattct ttttcagtcg aaaaatcatg ccatgagcat tcatgctttt gaccttaatt   21300
ctgatggagt gaatgaactg ataactggtt ggtccaatgg gaaggtaagt ttgaatagca   21360
aagttcaggt ataattcaga gtagtaattg tccaaggtgt attggctgta ggacttagaa   21420
cagtaacatt gggatgtaaa cttcagttcg ttccttggca atgtttttac atttaactta   21480
ataatcttga cacattcttc ctgctatcat tgtcaagagc tgcacagtga gagagtgtaa   21540
gtcttataag cggtgtttgg gggaaatctt cggggagatt ctgtctaaat ctcttatttg   21600
aagtgctgag aatccatcag ccagattgat tctaggtagt acaacagtaa aaaggagtt   21660 ttaaggaatt gtttgaatag ctcttttcca atacatcttc aaaactgcct gaaaacttag   21720
cactaatagg aagaatcatg ttagcatatt gttttctgag ctataacttt aaaataaaat   21780
ccttttgctt gctttccttt tttaacttca aatcagaatt ttttacagtc ttttggcaag   21840
tcaggattgt cttcttagaa gctgcctagg tagctgccag atctccatgg ataccatttg   21900
ccctcgcttt cttgtctgtc agtgttggat tgcctgaagg ggatcagcaa attcttatct   21960
tttcttcttt gatttatctt tactttctc tagcaccttg taagcattcc tttggtgtta   22020
cgtgaagaac ggattctaaa aagctgttat gttggtttct gcttcttcac ttagttttgt   22080
cattagtatg ggtactaaaa attataagac tgtatagttg cttattaaga aatatgaaag   22140
tctgtgaaat gggtgtctta gttggtttgg gctgctgtaa caaaatacca tagggtgggt   22200
ggcttataaa caacagaaat ttatttctta tagttctgga ggctgggaag cccccatcaa   22260
ggtgttggca gtttcagtgt ctggtgaggg accacttcct cataggagcc ttacagggtg   22320
gaaggggcaa gggatctctc tgggccttct tttatagggc actaatcctg ttcatggggg   22380 ctctgcccctt atgacctaat cacctctcac aagctctact tgccaatacc attcattacc   22440
ttggctaata ggattcagca taggaatttg tgggggcaaa acattcaga tcatagcagt   22500 ggatcatatt ttgagggaat ataaattatt atgactgact taagaattag aaaactacta   22560
gacttgaaaa cttgtcaggt taccttgaaa tataattgtt gacctagatg ttttttatagt   22620 taaatgctttt tgaaattta agggatttct attatgtaat gcgttcctga gcatgaaaaa   22680
gataagaaaa ttatataagt ggaaaaaccg attatctaca tctaacagaa atatacaaaa   22740
aggaaatata cagatccaac ttgtgaatac aggtgtgaaa atattaaata aatgctgcta   22800
```

```
gacaattaac tttgtctttt gtatgtcatt tgatgagttg gagggccatc ctttcctttc   22860
agggtaaaac ctcccagttg gattaagcaa aagatcagaa tatccacaga aatattaatt   22920
tgtagtcctg cttcttagtt agcaaatgag ccttcttatt tgctaaatat tgtggaaatg   22980
cagtggtaga agccattagg tagctaggct ttaactagaa agaagcaagt tcaggtcagt   23040
ctgagttaga gggctacatt aatgtgcttt gttaaaaatg caggtcattc gttctttcac   23100
aggctttagc attcataatt ttcaggcttc catgatgtta ttaatagcat taatacttga   23160
cagtgatata ctgtagacaa ggggtaggct gtaacctaaa ttactttatg ttttggttgc   23220
aaagttttgc ccagaagatt gtttatgaaa agacaaaact agtgagtagc attggtcatc   23280
gaaatgattg ctatgctaga ttttctgtag ctagccttt t gttgataata cctgtgtcct   23340
tgcctggaac ataatcatct ttttttttt t ttttgagact ggagtctcgc tttgtcaccc   23400
aggctggagt gcagtggcgc aatctcggct cactgcaacc tccgcctccc gggttcaagc   23460
gattctcctg cctcagcctc cctagtagct gggactacag gtgcgtacca ccacacccag   23520 ctaattttt t gtattttta g tacagacagg gtttcaccat gttagccaga atggtctcga   23580
tttcctgacc tcgtgatccg cctgcctcgg cctcacaaag tgctggcatt acaggcgtga   23640
gccactgtgc ccggcctcat aatcttcatt ttaagtgatg gtcacttatt atcacttttg   23700
agatgcattt gtttctgatc agtcatttat ttatttgttc tctctcttgg aaatgggaga   23760
cttagaggat aggagagctc tctaaagtat ctgaatagtt tttatgtgga agaggaactc   23820
ttaacagggt tgttgtaaaa ggttgcatgg tggaagactg ggctaactcc gtagtttctg   23880
aacttcagat tcaacatact ttatacattt atatataata aagatacaat ttttatatag   23940
agctaacatt tattacgtac ttctgtgtgt caggccctgt tgatatatgt taacttcatt   24000
aggcctcagt tatacccaat gggatatagt actgttaatt tctccatgtt ctggttattg   24060
aaccccagat gaaagacca agcacagaat ggttaagaaa cttgcaagat gctgtggata   24120
gtacgtggca gagctagatt ctgaacctga gcggtttggc cattaagccc atgccctttt   24180
gcactgtgct gtgtgtacta tatgtactgg ctcttagcag acccgtttct tcaagtgaag   24240
cattgtgtga aggcctatga aaaacagctt ttattaaaa agaaggaagc acagctggtt   24300
gaggctcttt agggtccctc ttggccccag cagtcatagg tatctcctga gaagttgtag   24360
ggcttcatag aatactcttg aaaactgcta gactaaatga cctttaaagc tgatttttat   24420
ttttaaattt tgtggttttt aaacatgtag cataagcaac ttttaaattt gtgttttatt   24480
tgtaggttga tgctcgaagt gaccgaactg gggaggtcat ctttaaggac aattttt ctt  24540 ctgcaattgc cggtgtggta gagggagatt accggatgga tggccacata cagttaatct   24600
gctgctcagt ggatggggaa agtaaattgg gatgagaaaa atccttaaaa agtcacgttt   24660
tccatttgat tgggtcaaaa tatcaggaaa tttcacctga agtatttgta ccgagatcct   24720
gtagttctaa taaattcacc aaagttgggg agaacttagg ttttt gtttt taagagcagg   24780 taattgatga cctaaaagta tacctggtta tacttgcggt ttttt ccttc tgttcagtcc   24840 ggggctacct gcctggcacg gctgagatga ggggcaacct catggacacc agtgcagagc   24900
aggacctgat ccgagagctg agtcagaaga agcagaatct gttgctggaa ctccgtaact   24960
atgaggaaaa tgccaaggta ggtgtaggtc ctaatgtgac caggtaatgg aggctgaaat   25020
gttgagactg accgggagga tcagcaaata tggaagaatg agagtgtcat tgccagggtg   25080
tggccttttt gccattgtca gaattgagag gggatatatg ctttcgtctt gaaatttcat   25140
ttccaggtag ttaaactgta gaaatgtttt cctgattgtt taaggacatt tcctgcagca   25200
```

```
ctatttattt atagcagtga aaacagctgg aagaaactta gatgttcgtc agcagtaggg   25260
agtatgtgct aaggaatatt aagcagctca aagaatgaat acttggactg atatggaagg   25320
atatctgtcg tcttaccaag tgacaaaagg caagaacaat atagaatgtc ttttatcttt   25380
ttcaaaaaca aacatgttaa aaacagacaa ctgtaaaaac tgtgtgtgtg catacagcaa   25440
actggctgaa atattccttt aatttgtcct gtaatgcatt actgtatttg aatttgatgt   25500
aacaagggaa tttgtttgct tactttaaaa gaacaatact tcaaaaatgt taaagtcatg   25560
atgggataca gtggaccata cccatagaaa gatgcaaggg tattttccca cagggccaga   25620
tagagcaagg gagcactaat gaggtgagtt ctctgaattc taaagaatca gattactata   25680
ataataataa tatgctggag gctctgtctt ttgaagctga atagcaatat tatttaaaat   25740
tgatattagt tcagtgtttt ggtgactgag taggaaatgg gtggggtgtt ttgcaggctg   25800
aattggccag tccactgaac gaggctgatg ggcatcgggg cataatccca gccaatacca   25860
ggctccacac cacgctctca gtcagcctgg ggaatgagac ccaaactgct catacagaat   25920
tacgcatttc cacttctaat ggtaagacag tactcacagc tggtatttag aggcacctgt   25980
gccatcttgg agtcattctt ttttttttt ttgagacaga gtcttcctct gtcttggctc   26040
actgcaagct ctgcctcccg ggttcatgcc attctcctgt ctcagcctcc caagtagctg   26100
ggactacagg cgcccaccac cacgcccagc taattttttg tattttagt agagataggg   26160 tttcaccgtg ttagccaaga tggtctcgac ctcctgacct cgtgatctgc ccacctcagc   26220
ttcccaaagt tggagttgtt cttaaactgt ttttactctt ccctgcagac accatcatcc   26280
gagcagtatt gattttgca gaaggaattt ttacaggtga aagccacgtg gtacatccca   26340
gcattcacaa cctctccagt tccatctgca tccctattgt gcctcccaaa gatgtccctg   26400
tggatctgca cttgaaggca ttcgtgggtt acagaagcag gtgacccttt gcaagtcaca   26460
gttcatttca ggacagcact tagaggaggg caagatgtat aaattttcca tatgcccagt   26520
ggattcttgg gggcctgaga accatttaa tggttctgtc tacccaaagt ttctcatgac   26580 ctttattc tcagtttga aacctgtaaa aagaaatgg aaaaactgat atgtaagttt   26640
aagatggttc tttttttttt ttttttttg agacagatte tageetttgte accecaggetg   26700 gagtacagtg gggcaatctc agttcactgc aacctctacc tcctgggtte aageaattet   26760 tctgcctcag cctcctgagt actgggacca caggtgccca ccaccacgcc cagctaattt   26820 ttgtatttttt agtagagaca ggagttcacc atgttggcca ggctggtctt gaactcctga   26880
cctcaggtga tccacccgcc ttggcttccg aaagtgctgg gattacaggc atgagccacc   26940
acgcctggct aagatcatta ttttctgttt ttagtcaggt gatctcataa tcaaaaaatg   27000
tttaattgat gatttgtcaa tttgtagttt tggccactaa aactacaaga gttaggatgc   27060
acctttatat tacagtcata cataacctca gctagtgaag aaaaactgct ctatttgtgg   27120
aagataagat acttttttaca tccccttttat gatattttaa acccttagtg catgcaggta   27180
tatatgtaga ctcatgctgt ctttaaatcc caaacctaat atattactgt agtactttaa   27240
ccctcaagtg ttttgggggt tccttcttaa gtgaaacccct taaatatcaa ttgatgaccc   27300
agaagtggct ttattttctg ggccttgcat tttgaaagaa cattctatac aaaacaattc   27360
tcttgtgttt cattgattgg ccatagcacc cagtttcatg tatttgaatc gacaagacag   27420
ctccctcgat tctccatgta tgcgctgacc agcctggacc ctgccagtga gccaatcagt   27480
tatgttaact ttaccattgc agaacgggca cagagggtga gtatctcgct tttctctttc   27540
aatgctttta cacagtagaa tcctttagat gttatttcat agaaagggaa aattacatta   27600
```

```
atgtgttata ttggtagcag taaatatgat atgaaagaat tctctaactt gggggtggct   27660
tgtaacctgt aataaaaata ttgctaaaat accttctctc actttgaaaa agcatctgag   27720
caatcctcag ttattggtga attcttacca gtgtttaatt cctctctttc cgttatggtc   27780
ttagtgtggt tgtcctggtg tagtatttca agaggaacct gcagcaagat gaaaagagag   27840
tgggacttgg agctaagaac gttttttggct ttaagtgcta cgttaactca ttaaattctt   27900
agtgatcttg gggaagtccc ctcaccagtg tgagcctcag ttttcttatc taataagtaa   27960
ggataatctt acccacctta ttgcgggggc ccgaggatta catgattggt gtaacagtag   28020
caccttgtac atttgaaagg actaatacca gtggacttta accttggctg ggctttggaa   28080
ttcttggtgg gactttttaa tcatgtagat tctcaggccc ctgcctggcc tgtggaacca   28140
cagactctat aggtgggccc ttccagaagg cctcatgggt ggttctcatg tggaacctgt   28200
gttgcaagcc actgcatggt gttactgcta ttaacattaa aacttatatt ttccttattg   28260
tgtggatata tctgtggtgt ttgcccatgt atacttcatt ttacatttct aaagaatag    28320 aatggaatgg ttttaagcac gctacattgt ccaggttata cccacagaag agctgttgtg   28380
taacagaatc agcatcatac ctgaatcatt tgtacattgc atataagact atgtctaagt   28440
agaagatgct atgaaatcat gtctgctgtg gggccaggca taattatgaa tgttacttaa   28500
gagcataggt gaggtgagaa aagggaatgt gactagtgtt ttagtatttt cttggtgtgg   28560
gatgaagtat aattcttttt ttttttctc aacaaagcag taaaactaga agaaggaga    28620 actcttccct caagaatggc tgtaccttca tatctagagg cacattaaaa aaaagaacgt   28680 ctgtaccttac aaaatggagg tcatttcatt gtgttcattt tcaaggttgt tgtatggctc   28740
ggtcagaact ttctgttacc agaagacact cacattcaga atgctccatt tcaagtgtgt   28800
ttcacatctt tacggaatgg cggccacctg catataaaaa taaaacttag tggagaggta   28860
atgtttaata tcacggggca tagatttctt ttttgaattt atttattcaa acacttagac   28920 catgaatga gagggcata gatttctcat gtggtgttta ccattcagtc caaagtgagg   28980
tgggggacat caatgtcaag gtcataaaac cacgttttgt tttattttt tcacatggtt   29040 taacttagtc tgttagtgtt accattttag acactgggt ataatttgga atagctgttt    29100
tctgcctcct tcccttcatc tcttccttgt ctaatttgga aagaattggg aatacagagg   29160
tcaacaaaaa cattttcaat gtttggatga ttttgtcatt taattctaa ggccagagga    29220 tttacctttt agctagctgc tggaaataat gcagtttgta atttctttga gagctaaact   29280
ttcctttttc aacactgcat atatatatat atgcacaata atttttgttga gtatgggaa    29340 attcaggtac tattttagct aagtttgtct aacatctgag gatgctaaac ttgtctattt   29400
tttctctggg tagatcacta taaatactga tgatattgat ttggctggtg atatcatcca   29460
gtcaatggca tcatttttg ctattgaaga ccttcaagta gaagcggatt ttcctgtcta    29520
ttttgaggaa ttacgaaagg tgctagttaa ggtgagggaa tgcggtagat gcatttgtga   29580
gaatgtggta gtctaataat atttgaggag attaatggta ctacaaatgt acttatgtta   29640
tagtgatgtt tcaagaatt tttgcaattc ttgaagtaaa aattgaacta gtattggaga    29700
gtttactact taaggattta ttttataaaa ggaagtgttt agctcctgag caccatgctt   29760
gctttgtttg gttaaagtg atgcatttaa atattaacat tttcctttgt tagctcttca    29820
tcttatttgt agtatctgct ttggtcttct tcagtttggg tctttccaaa acccaaatt    29880 caagataaaa gagcaaaata aagatgattc tgattggccc caaagtatac aatattccca   29940
ctgcaaatcc ctaaaatatt aatatgtgtg ttgtgggggc tcctggtgct aaagcatggg   30000
```

```
gaagattcac atggagtgtc gtgttgaaat tggaggcagc acagatgagt taacttgttg    30060
agacagagat gaaataacgg gaagtagctt aattggtata agcgaacagg ggaaagaagg    30120
gggtctctgt atctggtaaa tagtgtcttt tcatttgtct gggttcaaga agtttgtgag    30180
gccttttca  ttcctgagtg ttcatggtct ccaggtggat gaatatcatt cagtgcatca    30240
gaagctcagt gctgatatgg ctgatcattc taatttgatc cgaagtttgc tggtcggagc    30300
tgaggatgct cgtctgatga gggacatgtg agtatttgtc atggttagta caggtgcagg    30360
gttaaaaatg tgagcagtat ggaatagcaa ctctcagatg ttaccaatag aagtataaat    30420
tgttacagtg actttggaaa ataacttggc attatcagta aagttgaaaa tgcatgtcct    30480
ctatgaccca gcaattctat tcctggttta tagcttaggg aaagttacag cttagttata    30540
tgtatgctta taaccagga  tatttatata agaatatttg taaaggcatt gtttataaaa    30600
atctcaaaat ggaaacaatc caaattagca tgaacagtgt agcgacagtg gatgaattgt    30660
gatatattca tgcaatggaa tactacacag cagtgagagc acatgaatct ccatgacaca    30720
taagagcaag gaaaaatctg ataagcataa tggacactga aagaagacag acttaaaaga    30780
ctataaaatg tatccgtgtg tatagttaga gaaaagagta aactatagtt tgggaaacat    30840
gcaataaata aaaatataaa ttcagggaag agattatcat ataagatagt attttctcct    30900
agagaaggag ggattatgtt cagaaaaaac acattgggaa acttcctgtc tgaagtcttg    30960
tttaacttca ttaaatattc tgaatttttc tgaatatgta acattttaca ataaaaaagt    31020
taagtatgta cagtacaggt cttccttggt gcttgctagg atgccaaatt taccttgcca    31080
ataaaatgta ctgaaaaaaa ttcagtaaaa tagttaacaa attatagatg aaatttatgt    31140
gtatatatta ggggcaagag ttcactcaga gtgctgcttg tgttttttcc tgagacgcct    31200
gaattattgg caaataatta taatggtttt gctcagaggt aaatggtttt taaaataatt    31260
gtattgttga aaatttcaaa cacatacaga agtacttaaa tataatgatt tcatatatac    31320
cacccaccca acttcaacag ttatcaacta aagactgatc tttttttcatc tctacactca    31380
ccctcttttcc ctcccaggca ctagataatt ttgaggcaaa ttttggacat tgtgtaattc    31440
tagccacaac tatttcagac aaagggcctt tcaatatcat atatatat  atacatatat    31500
atacacacac acacacacac acacacatat atacacacgt ctgtataaaa atcacaatgc    31560
catatcacac ttagaaaaat ttacaataat tgcttaatat tacaaatacc tcatctgttt    31620
agatgttccc agttgtctta taaatgtgga catgtgtgtt ttaagttggc ttgctcaaat    31680
caaaatccag atcaaagtcc atacattgga tttggttgga aatcgtttaa tcttttaatc    31740
cacacttttg cttgcccact cagtctcttc tctccttctc ctgtggggtg ccattttgga    31800
ttttgctggt ggtatccttg tggtaatgtt tagtattatt cttctgtccc ctgtatagaa    31860
agataatggt agatctggag gcttgattag attcaatttc aaattttggc aagaatactt    31920
cgtgagtagt gttgtttact tccatgagga agcatgcaat ttttgattgt ttctttttat    31980
gatattatca gccattgatg atcattgcct agattcatta tttctttttgg ggtttgcaaa    32040
atagtgatat tctaattctg ttattctttt cttcatatat tagttgaaat acttctatga    32100
aaaataatgt tccctcatga attaatgaat tatttggttc cctgaggtac agtttgtaca    32160
ggaaagacag tttctttatc agcttttaaaa taatgtgttg atctccagca tgcactaggt    32220
gaccaatgag attttttaagt ccttacatac tcatgtattt gaacatattt aatgtgtttc    32280
aatttatatc tgttattatt aatttttatg gctagttttt ttttttttttt tcgagacgga    32340
gtctcgctct gtcgcccagg ctggagtgca gtggtgcaat ctcggctcac tgcaacctcc    32400
```

```
gcctcccggg ttcatgccat tctcctgcct cagcctcccg agtagctggg actacaggcg  32460
cccgccacca agcccggcta attttttgta ttttcagtag agacagggtt tcaccgtgtt  32520
agccaggatg gtctcgatct cctgagctcg tgatctgccc gcctcagcct cccaaagtgc  32580
tgggattaca ggtgtgagct actgcgcccg gccttttacg gctagatttt ccagtctgtg  32640
ggcaatggaa gtctctttag gttggataca gttacctttg gacatggtcc cattaatttg  32700
gttggttctt tgttttcttg tatgatgaaa tgtttcaggc ttatctggta catttcccag  32760
tcttcatatg gaaccagcca tttctctcga gtcctggttc ttttacatga gaaatggtat  32820
ttagagatca tggtctgacc actaaagatg ttcattgcta ctgggttgat tattgttttt  32880
aggccttttc aatgcgtaga gctaggaatt ttttttttca atgagaaaat atgagttcat  32940
actatttacc attcagattt atgaatatag gctcttcgat tttattactg cgcctcttct  33000
ctctcacatt gaaaatcatg gcttcaggtt gggcacggta gtttacactt gtaatcccag  33060
cactttgcga tgctgaggtg ggaggatcac atgagcccag ggattcgaga ccagcttggg  33120
caacatagtg agacccagtc tctgcaaaaa aaaaaaaaa aaaaaaatt agctgggcat  33180 agtggtgcat gcctgtagtc ctagttactc aggaggcaga ggtaagaaga tctctggaac  33240
ctaggagttt gaggctgcag tgagctatga tcatgacact gcaatccagc ctgggatgac  33300
agagcaagat ctcttaaaaa aaagtggggg aatatcatgg ctccaatcag tatcaacata  33360
actatttgct tcattttaca gcacagacac aacatttaag aatattagcc aagttgttat  33420
caacaatatg attgctgaaa acagtttaag attttttgtg tgttaattct ttgtgtcttt  33480
agggcatatc ccagcaggga gtttccgtca aattactgta tcttaaaatc atttgagatt  33540
atttctcttt tggttatgcc acagatttga tagagagtta ggttcattgt cttattttgc  33600
tctcagtttt ggaggattgg catttttacc ttttggtttt aattctatta catatttact  33660
aaaacctttt tgtaattcca agttagatc tataagacag gcatgcacgg aaaagtctaa  33720 cttttccattc ctgtgacctt cattctgttc tctcccttt actataaata accagttgaa  33780
catttaagta tatatatgca gatacacaca gatatataca cacacacccc tcttcatgtc  33840
ttagattaag tcatagtatg tatatatctt tttctccacc ttggtttttt tttttttttt  33900
tttttttttt gagacaaggt cttgctgtca cccaggctgg aatgtagtga tgcaatcaca  33960
gctcactgca gcttcaacca cccgggctca agggatcatc tcacctcagc ctcctgagta  34020
gatgggacta aaggcatgag ccaccagccc ggctaatttt ttatttttt gtagagacag  34080 ggtctcacca cattgcctgg gctggtcttg aactcatggg atctactgat cctcccacct  34140
tggcttccca agtgctggg attacagatg tgagccactg tgtccagcct ccaccttgct  34200
ttttacattt aaaatatatc ttggagattt ctccaccatg gtgtagagaa atacatctca  34260
tttgtcttta cggctacata gtactccatt ttctggctgt ttttcagcca gtttcctcta  34320
tttggattgt tttttttta ctgtagataa tgcttaagtg aatagttttg ttacgtaaat  34380 cttttatat ttttgccagg atagtttgag aaaaaggctt aacaaatggg attactgcag  34440
taaatgatac atgcatacag aattttgcaa ggtcttgtca aattctccat aggtgttacc  34500 tcatttgta ttcccataag caatgtatga gattgcctgt ttctcttcag ccttgccagt  34560
ggagtttgtg gcatactcc aggggatgag aaatggtctc ttagttttaa tttttatttt  34620
ttaaatttta ttttattgtg gtaagaccac agcatcagat ctaccttctt aacacatttt  34680
taagtgtata atacattatc gttgactata ggtgcagtgt tgtacagcac atctttagag  34740
ctgattcttc ttgcttaact gaaactattg gtaagcaaat tcccatttct tcttcccctc  34800
```

```
tttcaactat cattctactc tttgatttta tgaatttgac tattttagat actccatgca   34860
aatatataat atttgtcctt ctatgactgg cttatttcac tcagtgtaac atcctcagag   34920
ttcgtccatg ttgtcacata ttgcagaatt tccctctctt ttaagactga atagtgttcc   34980
attgtttata tgtactaaat tttctttatc cattcacctg ttgatgaaca tttatgtttt   35040
ttccacatgt tggttattgt aaatagtgtg gtgatgaacg tgggagtgct aataggtctt   35100
cagggtcttg tcttcagttc atttggataa atacccggaa gtgagattgc tagatcatat   35160
atggtagttc tattttttaat tttttgatta cattttttaat atttaatcat taaaaattaa   35220
aaatttaaat tttaatatt taatcattaa aaatttaaat tttaatatt taaatgtttt   35280
ccatagtggc tgcaccattt ttcattgtaa tcaacagtgt acaagggttc cagtttctct   35340
acatccttgc caacacttgt tgtctttttt ttgataattt tcatcctgac aaaggtgaaa   35400
tgatacttca ttgtggtttt gatttgcatt tccctgatga ctagtggcat tgggcgtctt   35460
tttatatacc tgtcggtcat ttgcttttct tgtttggaga aatttctatt caagtcccta   35520
gctcattttt taattggatt actagtgttt tttttttttt ttttttttgc tgttgagttg   35580
taggagccat ttattatgtt cagtattggg cattttttcat tgttttaatt cagggccatt   35640
tccatttctt ttttgtgtga actatttgtc tgtttacata tcaggtactg ttgtagtcca   35700
ttttgtgcct ctataacaga atacccgaga atgggtaatt tataaaggaa agaagttgat   35760
ttagcttatg ggtctgtagg ctgggaatta caagaaacat ggcactggca tccgcttgac   35820
ttctgttgag ggccatgtgt gaagtcaaaa catggcagaa aaggtcaaag agagagggga   35880
catgtgtgaa gaggcaaagc ctgaggggtg ccctaacttt ataacaaccct gctctttga   35940
taacttcatt cctgcatgag cgagaactca ctcctgagag atggcattaa tggcattaat   36000
ctattcatga gggatctgcc cccatgaccc aaacactccc tactaggccc acctcccaac   36060
actgctgtgc tggcatttca acttcaacat gagttttggc ggggacgaac cacatccaaa   36120
ccatagtggg tatattaatc tcttacgtgt gatatgagtt gcaaatatgt tttccggagt   36180
ttgtcatttg ggttttccct ttgcttagat ttttaaaaaa ttttgcttta atgggccagg   36240
cgcggtggct cacgcctgta atcccagcac tttgggaggc tgaggcaggt ggatcatgag   36300
gccaggagat cgagaccgtc ctgactaaca tggtgaaacc ctgtctctac taaaaataca   36360
aaaaatcagc cggtcgtggt ggcgggcgcc tgtagtccca gctattcggg aggctgaggc   36420
gggagaatgg tgtgaacccg ggaggcggag gttgcagtga gctgagatcg caccactgcc   36480
ctccagcctg ggtgacagag tgagactcca tctcaaaaaa aaaaaatttt gctttactgt   36540
tggttttacc ttgtaagagc ttttaaaatt ttgtatatag tcaaattata agaaaatttg   36600
actacattaa gaaaatgtaa gtcatttttct taatactttta tttatttatt tttgagacag   36660
agtctcactc tgttgcccag cctggagtgc agtggcgtga tctcggctca ctgcaacctc   36720
tgcctcccag attcaagtga ttctcctgcc tcagcctccc aagtagcgct accacacctg   36780
gctgattttt gtattttttag tagagacgag gtttcaccat gttggccagg ctggtctcaa   36840
actcctgacc tcaggtgatc tgcccgcctt ggcctcccaa agtgctggga ttacgggtgt   36900
gagccactgt gcccagccac attttcttaa tacttttaca ttttgaatta ctgttagaaa   36960
agttttcttt aacagcaggg tatagagtaa ttcatctgtt ttcctttagt acttgtatat   37020
tttgcttttt tacattaagt ctctgttcca gttggagttt atcctggtgt tcatataaat   37080
aataaactca gttttatcat ttttccttatg actatcacat tattattata ttattattat   37140
ttttgtgtgt gtgtgtgtgt gtgtgcgtgt gtgtgtgtgt gagataggt ctcactgtgt   37200
```

```
cacccaggct ggagtgcaga gagatcacag ctcacagcag cctcgatctc ctgggctcaa   37260
gttatcctcc cacctcagct gctggagtag ctgggactac aggcgtgtgc taccatagcc   37320
agctaatttt tgtgtagacc cagggtctcg ctctgttgcc cagactggtc ttgaactcct   37380
gggctcaagc gatctgcctg ccgtggcctg tcaaaatgct gggatttcag gcgtgagcca   37440
ctgtgcctgg ccacattgca ttattttaat actactactt ttttttttc tttgagatgg   37500 agtttcgctc ttgttgccca agctggagtg caatggcgct atcttggctc actgcaacct   37560
ctgccttcct ggttcaagcc attctcctgc ttcagcctcc cgagtagctg ggattacagg   37620
catgcgccac catgcccagc taatttttt tgtatttta gtagagatgg agtttcacta   37680
tgttggccag gctggtctca aactcctgac ctcaggtgat ccaccaacct cggcctccca   37740
aagtgctggg attacaggtg tgagccactg tgcccagcct gatactactt cttttaaagt   37800
tcatcatgct tacaatgatt tcagatactg cccttatcat atatcatatt tctgtacaca   37860
gttgaatcta tttctggatt ttctgtacta ttccattggt ctgacttgtc acttcatttg   37920
acaatatcat tcttttttaa aaaaaattat tttgagacag aatcttattc tgttgcccag   37980
gctggagcac agtggtgtga tcacagctca ctgcaacctc ggcctcccag gtacaaggga   38040
tcctcctacc tcagcctcct gagtaggtgg gactacaggc atgtgccacc acacccagct   38100
aatttttttt tattttggt agagacaggg tctcactata ttgcccaggc tagtctcaaa   38160
ctcctgaggt taagccatcc tcttgcctcg gccattttt tttttaatg tttggctggg   38220 tgcagtagct tatgtctata atcccagtgc tttgggaggt tgaggcatga ggatggcttg   38280
aggccaggag ctcaagacca gcctgggcaa tatagcaaga ccccatctct aaaaaagaaa   38340
atataaattt cattgtgata ttctgaaata catatttgat cttcaaccct gtttcctgac   38400
ataataactc ctaaaatctt aggctctcca aagtgatgtc tttttgtatg ctattgattg   38460
gtttatggct ggcagctcct aggtagcttc aggatagggg tcagtcacca gaacgaccaa   38520
ggcaggatta gaggattggg actttctgcc caccctctc ccaacctcca gggagtggag   38580
aggggctgag agttaagttg atcacctatg ccagtggtt tagtcagtca tgcccaaata   38640
atgaagattc catcaaaacc caagggaca gcattcagag attttctaga catctgaaca   38700
cacagagttt cctgaaggtt gatgcaccta gggagggcat ggaagctcca agcgccttcc   38760
ctaatacttc gttctatgca tctcttcatc tgtatccttt gtaatatcct ttataataaa   38820
ctagcaaatg ccattaagtt tccctgggtt ctatgtactg ctctagtaaa ttaatcaaac   38880
ccacagaggg ggtcatggga accctaactt gaagcagatc agtcagaaat tctggcagcc   38940
tgaacttgtg atatgtatct gaagtcaggc agtcttgtgg gactgagccc ttaatctgtg   39000
agatctgaca gtgtctccgg gggaatcgtg tcggaacgga attggaggac acccagctgg   39060
tgtctgctat agaactgatt gttttcttgg tgtgtgggaa aaacctccac acagttgagg   39120
acagaagtct tctgtgttga ttgttgtggt gtggagcag aggaggaaca gtttgttttt   39180
ttccccactc atggtgaact acacaatgtg aaatttacca tcttaactac tgtatactac   39240
ttttagtgta cggttcagtg gcattaaata cgttcataat gtgtaaccat caccaccagc   39300
agcatctcta taattcttta tctcttaaac ctgaaactct gtacccgtta aacagtaact   39360
acccattctc ccttccctt agctctggca actaccagtg atggtgccat tctttcatgt   39420
atggatgttt tgtatgtttc aatatctggt gtgggtagtg cccgtccc aaccctgtt    39480 gcttttcttt ttcatggttt ttcctagcta cttgtgcttg tttgttcttt ccaatgaatt   39540
tcatcagcaa ttttttgtagc tccgtaacaa aaataggtat tttaattgag atgatgttaa   39600
```

```
atgcattaac ttagggagaa ctgatgctgc tgcagtgatg tttggtcttg ctagctaaga    39660
acatgctatg tctttatatt tgcttaagcc atgttttgtg tctttctgga gtgctttcat    39720
ggtttactct tgtagatact ggatgttacc aattttaagt ttatgcttag gtattttctg    39780
tatttttaga caattacgaa atattttata attgtaaata ttttttacat tatcttattc    39840
tataattatg gttttgtgtt tgtacatatg aacactgatt tttatctgtt gattttataa    39900
tgtgcccttt actaactatc ttatagtttt tccagatgta ttcttgtatc atctgtaaat    39960
tgagatagat atttgctctt tttggccaac tatctgtagg gtccctagtt tctctatctc    40020
tctatctctc tcttaagtca aaatggttg ctggctttag gcatttgatt gcaaaatgtc     40080
aacatttgtt ttttttttta aatcaaatta attgatatat aactcataca tgcagaaaat    40140
ttatgctttt aaggtttaca gtttaatcaa ttttgagaaa cttatgtaat catgttgcta    40200
ctactacaat cgagatatag gatatttcta tcactggccg ggtggctcac acttgtaatc    40260
ccagcatttt gggaggccaa ggtgggtgga tcacttgaag ccaggagttc gagaccagcc    40320
tggccaacat ggtgaaaccc agtctctact aaaactacaa aaaattagcc aggtgtggtg    40380
gcgggtacct gtaatcccac ctattcagga ggctgaggca ggagaatcac ttgaacctgg    40440
gaggtggagg ttgcagtgat ccgagatcgt gccattgcac tccatctagc ttactgggca    40500
acaagagcaa aactccatct caaaaaaaaa aaaaaaaaa aaaagaata tttctgtcac      40560 tcttgtgact gtttgtatca atacctcttc taacctccag ttcctggaaa ccactcatct    40620
tatttctttt cctgtagttt caaccttttc aaaataccat ataaatggaa tcatactgta    40680
tctatatcta tatatccttt tgagtctggc ttcattcact tacataatgt cttagagatt    40740
catccatgtt gctgcatgta tttgtagttc ctttttttatt gctgaatagt attccattgt    40800
atggatatat gatatttatc tattcaccaa ctgaggataa ttgggttgtt tccagacttt    40860
ggtgagtaga ataaagctgc tataaatact tgcatacaag ttttttatag acataggttt    40920
tcatttctct tgggtaaata ccttacaatg ggattgctgg gtcatacatt gtgtgtttaa    40980
ctttataaga aactgccaaa tcacctgtca aagtagttgc agcttttgt atttctgtcc     41040 acaatgcatg aaagttccag ttgtcccaca tctttgctag catttggtat cttcagctat    41100
attttctttt agttattttc attgttgtgt agtatagatc tcatttctgt tttaatttta    41160
tgactttgtt ttaaaccttt gataaaatac aaggctgagt tgtcaaccag gccactttag    41220
tctaatgaat attcatctga aacttggaag gtgggctgtc accttgctca cttgtcccta    41280
ctcccagcac agtgggcttg agaattctta accacctaaa tcaaccattg accagtaacc    41340
aaggaaggcc acttgtcttc tgtttatttg gaaggaaaag aatattttta tggaacttat    41400
ccgtattttc aaagcaaact agcagttact cgatttttaat gaaatatag cttaaaaatg    41460 gtgtcttttc tttgtatgtc taagaaattt gcaagttttt cttaagcttg ccatatcaac    41520
atgaaatgat gtcaaatttc tactgatttg cacaggaaaa caatgaagag tcgttatatg    41580
gaactctatg accttaatag agacttgcta aatggatata aaattcgctg taacaatcac    41640
acagagctgt tgggaaacct caaagcagta aatcaagcaa ttcaaagagc aggtcgtctg    41700
cggggtaagt ctcttttcat aacactgcac tttgatctgt aatgttttg gtggaactca    41760 ttgaagatgg tggtagcatc caataattca tattggggct gaaagtagca taccttttcac   41820 actccagagc tggcaccagt cacttatgtt tcagtcagtc ggcctagtgt ttggcttttg    41880
tctccggact tcaagggag agaaaacctt cagctccttt tcttagacct tcctgcatcc     41940
tctaaagaaa aacctactat atataaccca aaggaaatat ataaacatat atatataaat    42000
```

```
aaaaccatca aggcccaatt agcaaaaaag agactgaaaa ttaatgctaa gtgtctaact    42060
taaaaattta gaaagaaaca ataggataaa cccaaggaag cagaaatata gccagagatt    42120
tatacctgaa ttctgctgtt ttgggtcgat gctttgactt ctttagaaat aatctttgct    42180
aggtgactat gagctttgat cctttctgt aaaactgact gttggtttct aggtttgaga    42240
cagtctctaa gtcagttttt tcaataattc cctcaccaag ttattttttt tagggaatgg    42300
taagataaat catatttcaa gtataactct tttccctcct ggttttatgt tgttttaaaa    42360
ctgacgtcta atttataat ttcatgtcta acaatctttt ggttcctgat gtttcttctt    42420
atgcagttgg aaaaccaaag aaccaggtga tcactgcttg tcgggatgca attcgaagca    42480
ataacatcaa cacactgttc aaaatcatgc gagtggggac agcttcttcc taggtgagga    42540
aaatacaggt catgaagttc ctggcaaaga ttttctgtta aaaacctatg ctggtttgct    42600
ttggatcaca ccctggtgaa cccgggtgc taagaatgaa ataaccttg gtgagttgta    42660 caaattaaag acaaagaact acatgtgaag atagacttgc tttctatttt taaatcagta    42720
gtagtactgt tgctgaataa tactaggttt ttatggaata ggatgaatgc ttttgaagta    42780
ttagggcttc agagtccaat tttgcttatt tatggtatat aaatacatat tttttcttg    42840 aaattgcaat tgagtttgta cttttcaaat agattatcta ctttttcatt aaaatgtaaa    42900
gatgttaaac tttgtgttga ttgattataa aatcaccacc aaatcagaat tgcccatttg    42960
tattttgtag tagagaaaaa caaaaatgtg ggctgggcac agggcttatg cctgtaatct    43020
agcactttgg gaggccaggg cgggcggatc ataaggtcag gagatcgaga ccatcctggc    43080
taacacggtg aaacccgtc tctactaaaa acacaaaaaa ttagctgggc atggtggcac    43140
tcatctgtag tccaagctac ttgggaggct gaggcaggag aattgcttga cccgggtgg    43200 cagaggttgc aatgagccta gattgcacca ctgcactcca gtctgggcga cagcaagact    43260
cccgtctaaa aaaaaaaaaa aaaaaatat ttgggctgag ctcagtggct cacacctata    43320
atcctagcac tttgggaggc caaggcgggt ggatcccctg aggtcaggag tttgagacca    43380
gcctggccaa catgatgaaa cctggtctct actaaaaata caaaaaatta gccaggtttg    43440
gtggtggaca cctacaatcc cagctatgca ggaggctgag gcaggagaat tgcttgaacc    43500
caggaggtgg aggttgcagt gagcaagatt gcaccactgc actccagcct gggtgacaag    43560
agcaaaactc tgtctcaaaa aaaaaaaaaa atgtggatat ttgggatttgt gtgctttta    43620 atcactgaaa gatgggtgca aacaacaaat ttacattaag gaagagtcaa tttagagtga    43680
ttactttgtt gggctaatgt tagctgctgt aacaaataga cctcaaaatc ataatgactc    43740 attttttcatt tattatgtaa ggatttctcc atagttatgc agggacccag gttcctttaa    43800
tcatgtggct ctgtcatccc ctaggacaaa cttttctacc tgagttcact aaaggactaa    43860
gcctaaggaa aaaggtttgg gtgactagtt tcacattcag tacatacagt ggagggaggt    43920
cttagggcag tggggcttta ttatctcact tggaacacta tttgacaagg gctgtcctag    43980
ggccttgtgg ttatttacag ccatgtacca gataatgaag tttaggtcac cataagatta    44040
taatactgta ttttttactgt acctttgtgt ttagatatgt ataattacac aaatacttag    44100
cattatgtta cagtttccta cagtattcag tatagtacca tgctgtacag atttgtaggc    44160
tgggaacaac aggctatact gtatagccta ggtgtggagt aggctatacc atctaggtgt    44220
gtataagtgc acactgtaca atgttcacat gatgacaaag tagcctaaca atgcatttct    44280
cagactgtac tgctgttgtt agcagagcat gaccatatag ctgagccggt agaagagagt    44340
aagagggaaa catgtcttct tcttttaaaa gtgtggtctg aaagtagcac actatcattt    44400
```

```
ccattcagaa ttccattgag tcacatgacc acatctgcag gggaggccgg gagatggaat    44460
ctagctgtgt gcctgtagga acgctggtat ttgtgccaat agctagcagt ctcttcccta    44520
ggaaaaattt cgccctaacg tagatttcag gactggttta atgagtgaaa cttcagttag    44580
ttttaatatc ttaatagctg tttaggggaa gtggagcatt tccctgaggt tagtaaacat    44640
taattttatt gattttgatg tggccacttt acgatggccc ctcctatatc tgaaatttaa    44700
gccttatgga gtcctaatta tgagaatatg ctaatacttt tgtttttcat tttcaaccta    44760
taaactcaag agataatcca catacactgt attattttca atctccaaag tagtaaagta    44820
tcatcgtaaa tctgcctcac acagaggttg ctgtgagccg agatcatgcc actgcactct    44880
agcctgggtg acagagggag actccatctc caaaacaaaa ataaataaat aaataaataa    44940
atgtgcctca cagaggagga aactgaggca taaataacct ccttttcagg tcacagagtt    45000
agtgacctgt gtgacctgtc tagtgactca agaggaaact tgagtcctac tgttgagtct    45060
ttgttttaac catagtctaa tttataccat ttgagattaa aatctctagt tggtgctagt    45120
tttaaattat ataatgccat tcattttag ggagtctaat aacataatct catcaaaggt    45180
cactctgttg ttctttagct aaaaaacttc cttcttagac ctaaaaatac tcatggccag    45240
gctagaaggc attgacctgc agcaagacat attaagttgt tctgattcat aggttatttt    45300
cacagtaatt tgatcctgtt gatgttggtg tctgtttcac agatgaggct ctgagctcta    45360
agacagagtg tcctgtacag ggtcccacag ctgggtaagc cctggtgtga aggaggtgtt    45420
ggaaacaagt agtcacggcc tcttctactc caaacttccc aagcaagtaa agactggccg    45480
aagtgaaaac attcataaaa catgcaacta cctttttcc cccaacttag aactcatcct    45540
gttcagctta ggagtgagga aaaactggac aaggagagat gagtttatca gtaacttctc    45600
tattttgttg ccatatgttt ctatcctgat agaatctgag tacttctaga agctacagca    45660
aagctgtatt tcactgctga attacattga agctttaagt gagcactgag ctgtcattta    45720
aaagctgact ttgaggattt tgatatctga gagaaagctt tcagtaccat aattcaggtt    45780
ctgaggattt ttaagagtat aatttgtatt atttcccacc atgactgcct atccagtac     45839
```

BARDET-BIEDL SUSCEPTIBILITY GENE AND USES THEREOF

This application is a continuation of U.S. patent application Ser. No. 11/370,242, filed on Mar. 7, 2006, which is a divisional of U.S. patent application Ser. No. 10/025,187, filed on Dec. 18, 2001, issued as U.S. Pat. No. 7,008,782 on Mar. 7, 2006, which claims priority to U.S. Provisional Patent Application Ser. No. 60/256,900 filed on Dec. 19, 2000 and U.S. Provisional Patent Application Ser. No. 60/258,949 filed on Dec. 29, 2000. The entire text of the above-referenced applications are specifically incorporated herein by reference without disclaimer.

The government may own rights in the present invention pursuant to NIH grant number R01-EY-11298.

BACKGROUND OF THE INVENTION

1. Field of the Invention

The present invention relates to the fields of genetics and molecular biology. More particular the invention relates to the identification of a gene on human chromosome 16 that is involved in Bardet-Biedl Syndrome (BBS), designated here as negevin (ngvn). Defects in this gene are associated with a variety of clinical symptoms including diabetes, high blood pressure, renal cancer and other defects, retinal degeneration, congenital heart defects, limb deformity and obesity.

2. Description of Related Art

Bardet-Biedl Syndrome (BBS) is a rare, autosomal recessive disorder characterized by mental retardation, obesity, pigmentary retinopathy, post-axial polydactyly and hypogonadism. A high frequency of renal abnormalities is also associated with this disorder. The mental retardation is often mild. Obesity begins early in infancy, and complications of obesity including diabetes mellitus and hypertension occur later in life. The associated retinal degeneration is usually severe and most patients become blind prior to 20 years of age. A recent report also provides evidence of an increased incidence of renal cell carcinoma (kidney cancer) as well as kidney malformations in BBS subjects.

The incidence of BBS varies between populations. A relatively high incidence of BBS is found in the mixed Arab populations of Kuwait and the Bedouin tribes throughout the Middle East, most likely due to the high rate of consanguinity in these populations. A relatively high frequency of BBS has also been reported in New Foundland.

BBS has been shown to display a remarkable degree of non-allelic genetic heterogeneity. The disorder was first shown to be genetically heterogenous based on mapping studies performed in large inbred Bedouin kindreds from Israel. The large number of traditional consanguineous marriages within these groups make it possible to identify inbred kindreds with multiple affected individuals that are large enough for independent linkage analysis.

The first BBS locus (now referred to as BBS2) was mapped to chromosome 16 using a large inbred Bedouin kindred. Genetic heterogeneity was demonstrated when a second Bedouin BBS kindred did not map to the chromosome 16 locus. Subsequent studies in the second Bedouin kindred revealed linkage to chromosome 3 (BBS3). A third Bedouin kindred showed linkage to chromosome 15 (BBS4). To date, studies have demonstrated the existence of six BBS loci, and a seventh BBS locus has been postulated based on the fact that a few small BBS pedigrees do not appear to map to any of the known loci. A locus on chromosome 11 was assigned the designation BBS1 based on the fact that it appears to be the most common cause of BBS in some populations.

Recently, the first BBS gene (MKKS) was identified independently by two groups that hypothesized that mutations in the gene causing McKusick-Kaufman syndrome (MKS) could also cause BBS. MKS is an autosomal recessive disorder characterized by post-axial polydactyl), as well as genital and cardiac anomalies. Mutations in the MKKS gene, a putative chaperonin gene, appear to account for approximately 10% of BBS cases. The mechanism by which mutations in the MKKS gene cause BBS has not been determined.

Interest in the identification of genes causing BBS stem from the pleiotrophic nature of the disorder, and the fact that identification of BBS genes may provide important insight into biochemical and developmental pathways involved in common complex disorders including obesity and diabetes mellitus.

SUMMARY OF THE INVENTION

Thus, in one aspect of the invention, there is provided an isolated and purified nucleic acid encoding a human negevin (NGVN) polypeptide. The amino acid sequence of SEQ ID NO:2 is exemplary, as are the nucleic acid sequences of SEQ ID NO:1 or SEQ ID NO:3. In addition, variants of the sequence included one or more of the changes selected from the group consisting of $T_{224} \rightarrow G$, $C_{814} \rightarrow T$, $C_{823} \rightarrow T$, $A_{387} \rightarrow G$, $A_{1413} \rightarrow C$, $A_{940}$del and 1206insA. The nucleic acid may further comprise a promoter, for example, an inducible promoter, a constitutive promoter, or a tissue specific promoter. It may also comprise a selectable marker, a polyadenylation signal and/or an origin of replication.

The nucleic acid may be part of a replicable vector, for example a viral vector such as a retroviral vector, an adenoviral vector, an adeno-associated viral vector, a herpes viral vector, a polyoma viral vector, a vaccinia viral vector or a lentiviral vector. The viral vector may be located within a viral particle. The vector also may be a non-viral vector.

In another embodiment, there is provided an oligonucleotide of about 10 to about 50 bases comprising at least 10 consecutive bases of SEQ ID NO:1 or SEQ ID NO:3, or the complement thereof. The oligonucleotide may be 10, 15, 20, 25, 30, 35, 40, 45 or 50 bases in length, and may have 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive bases of SEQ ID NO:1 or NO:3. The oligonucleotide may encode or be complementary to a splice junction or regulatory region of SEQ ID NO:3. The oligonucleotide may encode or be complementary to bases 224, 814, 823, 387, 1413, 940 or 1206 of SEQ ID NO:1. Also provided is human NGVN promoter isolatable from SEQ ID NO:3.

In still another embodiment, there is provided an isolated and purified human NGVN polypeptide, for example, comprising the sequence of SEQ ID NO:2. The polypeptide may also have one or more of the changes selected from the group consisting of $Val_{75} \rightarrow Gly$, $Arg_{272} \rightarrow Stop$, $Arg_{275} \rightarrow Stop$, and $Ile_{123} \rightarrow Val$. The polypeptide may comprises less than the entire NGVN sequence, for example, only residues 1-313 or 1-401 of SEQ ID NO:2. The NGVN polypeptide also may be fused to a non-NGVN polypeptide.

In yet another embodiment, there is provided a method of expressing a NGVN polypeptide comprising transforming a host cell with an expression construct encoding a NGVN polypeptide and culturing said host cell under conditions supporting expression of said NGVN polypeptide. The host cell maybe a prokaryotic or a eukaryotic cell. The method may further comprise purifying said NGVN polypeptide. The expression construct may comprise an inducible promoter, and the method may further comprise providing to said host cell and inducer of said promoter.

In still yet another embodiment, there is provided a peptide of 8 to 50 residues comprising at least 5 consecutive residues of SEQ ID NO:2. The peptide may be 10, 15, 20, 25, 30, 35, 40, 45 or 50 residues in length, and may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 consecutive residues of SEQ ID NO:2. The peptide may be bound to a carrier molecule, for example, by a linker. Also provided are a monoclonal antibody and a polyclonal antiserum that binds immunologically to a polypeptide comprising the sequence of SEQ ID NO:2. The antibodies may be bound to a support.

In still further embodiments, there are provided a method of diagnosing Bardet-Biedl Syndrome (BBS), a method of diagnosing an individual genetically predisposed to obesity, diabetes mellitus, retinopathy, hypertension, kidney cancer (renal carcinoma) and other renal abnormalities, congenital heart disease or limb defects comprising identifying a mutation in a NGVN polypeptide or nucleic acid. The method may comprise identifying a mutation in a NGVN polypeptide, for example, using immunologic analysis with a NGVN-binding monoclonal antibody or polyclonal antiserum (e.g., ELISA, RIA, or Western blot). The method may identify a mutation selected from the group consisting of $Val_{75} \rightarrow Gly$, $Arg_{272} \rightarrow Stop$, $Arg_{275} \rightarrow Stop$, and $Ile_{123} \rightarrow Val$.

Alternatively, the method may comprise identifying a mutation in a NGVN nucleic acid, either mRNA, genomic DNA or cDNA. The method may comprise amplification of said nucleic acid, hybridization of said nucleic acid to a labeled nucleic acid probe, and/or sequencing of a NGVN nucleic acid. Again, the method may identify a mutation selected from the group consisting of $T_{224} \rightarrow G$, $C_{814} \rightarrow T$, $C_{823} \rightarrow T$, $A_{387} \rightarrow G$, $A_{1413} \rightarrow C$, $A_{940}del$ and 1206insA.

In still other embodiments, there are provided:

a method of screening for a modulator of NGVN expression comprising (a) providing a cell expressing a NGVN polypeptide; (b) contacting said cell with a candidate modulator; (c) measuring NGVN expression; and (d) comparing said NGVN expression in the presence of said candidate modulator with the expression of NGVN in the absence of said candidate modulator; wherein a difference in the expression of NGVN in the presence of said candidate modulator, as compared with the expression of NGVN in the absence of said candidate modulator, identifies said candidate modulator as a modulator of NGVN expression; and a method of screening for a modulator of NGVN expression comprising (a) providing a cell that comprises an expression construct encoding an indicator polypeptide under the control of a NGVN polypeptide; (b) contacting said cell with a candidate modulator; (c) measuring expression of said indicator polypeptide; and (d) comparing said expression of said indicator polypeptide in the presence of said candidate modulator with the expression of said indicator polypeptide in the absence of said candidate modulator; wherein a difference in the expression of said indicator polypeptide in the presence of said candidate modulator, as compared with the expression of said indicator polypeptide in the absence of said candidate modulator, identifies said candidate modulator as a modulator of NGVN expression; and a method of producing a modulator of NGVN expression comprising (a) providing a cell expressing a NGVN polypeptide; (b) contacting said cell with a candidate modulator; (c) measuring NGVN expression; (d) comparing said NGVN expression in the presence of said candidate modulator with the expression of NGVN in the absence of said candidate modulator; wherein a difference in the expression of NGVN in the presence of said candidate modulator, as compared with the expression of NGVN in the absence of said candidate modulator, identifies said candidate modulator as a modulator of NGVN expression; and (e) producing the modulator; and a modulator of NGVN expression produced according to the method comprising (a) providing a cell expressing a NGVN polypeptide; (b) contacting said cell with a candidate modulator; (c) measuring NGVN expression; (d) comparing said NGVN expression in the presence of said candidate modulator with the expression of NGVN in the absence of said candidate modulator; wherein a difference in the expression of NGVN in the presence of said candidate modulator, as compared with the expression of NGVN in the absence of said candidate modulator, identifies said candidate modulator as a modulator of NGVN expression; and (e) producing the modulator.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

Bardet Biedl Syndrome (BBS) is a debilitating genetic disorder that is prevalent in Bedouin populations, probably due to the high consanguinity observed therein. In order to identify the gene causing BBS2, the inventors used genetic fine mapping to reduce the size of the BBS2 interval on chromosome 16 from the previously reported interval of 18 cM. Fine mapping looking at shared haplotypes of affected individuals within the extended Bedouin kindred only made it possible to narrow the interval to approximately 6 cM. Therefore, it was decided to search for unaffected individuals within the extended kindred who had the complete affected haplotype on one chromosome, but were recombinant for the affected haplotype on the homologous chromosome. Two such individuals were identified, and the recombination events within these individuals greatly reduced the candidate interval to approximately 3 cM. The ability to narrow the disease interval using data from the Bedouin kindred made it possible to construct a physical map across the disease interval.

The identification of the BBS2 gene was aided by sample sequencing (approximately 1× coverage), as well as sequence data from the Human Genome Project. Analysis of this sequence resulted in the identification of a number of candidate genes within the narrowest interval. In order to determine which of these genes was the BBS2 gene, the inventors undertook to prioritize the genes for mutation screening based on a number of parameters including sequence homology or a putative functional relationship to genes in other known BBS intervals, as well as tissue pattern of expression. Although this approach yielded a number of high priority candidate genes, none of these genes proved to be mutated in BBS patients. The recent identification of BBS causing mutations in the MKKS gene provided initial speculation that a chaperonin gene might be found in this interval. A search of the available sequence in the interval failed to identify such a candidate gene.

Due to the non-allelic genetic heterogeneity of BBS, the strategy for mutation screening of candidate genes was to focus the search for mutations by direct DNA sequencing of DNA from a proband from each of two inbred families shown to link to the chromosome 16 BBS interval. One of the families was the large Bedouin kindred that was used to initially map and refine the 16q21 interval. Sequencing of probands from inbred families provided the advantage of looking for homozygous sequence variations compared to control sequence. Homozygous changes are more readily recognized compared to heterozygous mutations by direct sequencing. Sequencing revealed homozygous mutations in the negevin (ngvn) gene in each of the two inbred families. Each mutation was shown to segregate completely with the disease phenotype in the respective kindreds, and neither mutation was found in 96 control individuals. After the identification of mutations in NGVN in both of the linked families, the inventors screened an additional 18 probands for NGVN mutations. A total of 4 probands (22%) had mutations, a figure that is consistent with the proportion of BBS2 cases reported in the literature.

The conclusion that NGVN is the BBS2 gene is supported by a number of lines of evidence. First, it maps to the narrowed disease interval and has a broad pattern of tissue expression as would be predicted for a pleiotrophic gene. Second, it is found to have homozygous mutations in two inbred pedigrees, one of which is a frameshift. And third, it is mutated (both nonsense and frameshift) in a number of isolated BBS probands and small families. Together, the evidence strongly supports the conclusion that NGVN is responsible for the BBS2 phenotype.

The inventors have previously hypothesized that the identification of the first BBS gene would lead to the rapid identification of other BBS genes. In the case of MKKS, this has not yet proven to be the case, as NGVN has no significant sequence homology to MKKS and no currently known functional relationship. Despite this fact, the inventors hypothesize that a functional relationship does exist. It is possible that NGVN plays an unrecognized chaperonin role or is part of a chaperonin complex. Another possibility is that NGVN is a substrate of MKKS chaperonin function.

The identification of NGVN has immediate implications for the isolated Bedouin community that was used in the initial mapping and that has a high incidence of the disease. Population-wide carrier testing could now be efficiently performed to accurately identify disease gene carriers. Such a program would have the potential of decreasing the burden of this disorder in this isolated community. Detection of carriers might be particularly useful in this society since the vast majority of marriages are arranged. In addition, the present invention also provides the opportunity for therapeutic intervention, as well as drug screening to identify therapeutic agents. This and other embodiments are described in greater detail below.

1. NGVN Protein

The protein sequence for human negevin is provided in SEQ ID NO:2. In addition to the entire NGVN molecule, the present invention also relates to fragments of the polypeptides that may or may not retain various of the functions described below. Fragments, including the N-terminus of the molecule may be generated by genetic engineering of translation stop sites within the coding region (discussed below). Alternatively, treatment of the NGVN with proteolytic enzymes, known as proteases, can produces a variety of N-terminal, C-terminal and internal fragments. Peptides range from 6, 7, 8, 9, 10, 15, 20, 25, 30, 35, 40, 45, and 50 residues, such as those made synthetically, up to 100, 150, 200, 250, 300, 350, 400, 450, 500, 550, 600, 650, 700 and more residues, which are conveniently produced by recombinant means or by proteolytic digestion of full length NGVN. Examples of fragments may include contiguous residues of SEQ ID NO:2 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200, 300, 400 or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Variants of NGVN

Amino acid sequence variants of the NGVN polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within 12 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of NGVN, but with altered and even improved characteristics.

B. Domain Switching

As described in the examples, the present inventors have identified murine and rat NGVN, in addition to humans. An interesting series of mutants can be created by substituting homologous regions of various proteins. This is known, in certain contexts, as "domain switching."

Domain switching involves the generation of chimeric molecules using different but, in this case, related polypeptides. By comparing various NGVN proteins, one can make predictions as to the functionally significant regions of these molecules. It is possible, then, to switch related domains of these molecules in an effort to determine the criticality of these regions to NGVN function. These molecules may have additional value in that these "chimeras" can be distinguished from natural molecules, while possibly providing the same function.

C. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

D. Purification of Proteins

It will be desirable to purify NGVN or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

E. Synthetic Peptides

The present invention also describes smaller NGVN-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antigen Compositions

The present invention also provides for the use of NGVN proteins or peptides as antigens for the immunization of animals relating to the production of antibodies. It is envisioned that NGVN or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

G. Antibody Production

In certain embodiments, the present invention provides antibodies that bind with high specificity to the NGVN polypeptides provided herein. Thus, antibodies that bind to the polypeptide of SEQ ID NO:2 are provided. In addition to antibodies generated against the full length proteins, antibodies may also be generated in response to smaller constructs comprising epitopic core regions, including wild-type and mutant epitopes.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The term "antibody" is used to refer to any antibody-like molecule that has an antigen binding region, and includes antibody fragments such as Fab', Fab, F(ab)$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic NGVN composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/$m^2$) (Johnson/Mead, NJ), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified NGVN protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MCPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in E. coli.

H. Antibody Conjugates

The present invention further provides antibodies against NGVN, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anticellular agent, as may be termed "immunotoxins" (described in U.S. Pat. Nos. 5,686,072, 5,578,706, 4,792,447, 5,045,451, 4,664,911 and 5,767,072, each incorporated herein by reference).

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99m}$ by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) and ethylene diaminetetracetic acid (EDTA). Also contemplated for use are fluorescent labels, including rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

2. NGVN Nucleic Acids

Important aspects of the present invention concern isolated DNA segments and recombinant vectors encoding NGVN proteins, polypeptides or peptides, and the creation and use of recombinant host cells through the application of DNA technology, that express a wild-type, polymorphic or mutant NGVN, using the sequence of SEQ ID NO:1 and SEQ ID NO:3, and biologically functional equivalents thereof.

The present invention concerns DNA segments, isolatable from mammalian cells, such as mouse, rat or human cells, that are free from total genomic DNA and that are capable of expressing a protein, polypeptide or peptide. As used herein, the term "DNA segment" refers to a DNA molecule that has been isolated free of total genomic DNA of a particular species. Therefore, a DNA segment encoding NGVN refers to a DNA segment that contains wild-type, polymorphic or mutant NGVN coding sequences yet is isolated away from, or purified free from, total mammalian genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified ngvn gene refers to a DNA segment encoding NGVN protein, polypeptide or peptide coding sequences and, in certain aspects, regulatory sequences, isolated substantially away from other naturally-occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and engineered segments that express, or may be adapted to express, proteins, polypeptides, domains, peptides, fusion proteins and mutants of NGVN encoded sequences.

"Isolated substantially away from other coding sequences" means that the gene of interest, in this case the NGVN gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

A. Variants

In particular embodiments, the invention concerns isolated DNA segments and recombinant vectors incorporating DNA sequences that encode a NGVN protein, polypeptide or peptide that includes within its amino acid sequence a contiguous amino acid sequence in accordance with, or essentially as set forth in, SEQ ID NO:2, corresponding to the NGVN designated "human NGVN."

The term "a sequence essentially as set forth in SEQ ID NO:2" means that the sequence substantially corresponds to a portion of SEQ ID NO:2 and has relatively few amino acids that are not identical to, or a biologically functional equivalent of the amino acids of SEQ ID NO:2.

The term "biologically functional equivalent" is well understood in the art and is further defined in detail herein. Accordingly, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferrably about 81% and about 90%; or even more preferably, between about 91% and about 99%; of amino acids that are identical or functionally equivalent to the amino acids of SEQ ID NO:2 will be sequences that are "essentially as set forth in SEQ ID NO:2," provided the biological activity of the protein is maintained. In particular embodiments, the biological activity of a NGVN protein, polypeptide or peptide, or a biologically functional equivalent, comprises binding to one or more proteases, particularly serine proteases. In specific embodiments, the biological activity of a NGVN protein, polypeptide or peptide, or a biologically functional equivalent, comprises inhibition of the activity of one or more proteases, particularly serine proteases, through binding. A preferred protease activity that may be inhibited by a NGVN protein, polypeptide or peptide, or a biologically functional equivalent, is inhibition of the ability or rate of proteolytic cleavage catalyzed by the protease.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1.

The term "functionally equivalent codon" is used herein to refer to codons that encode the same amino acid, such as the six codons for arginine and serine, and also refers to codons that encode biologically equivalent amino acids. For optimization of expression of NGVN in human cells, the codons are shown in Table 1 in preference of use from left to right. Thus, the most preferred codon for alanine is thus "GCC", and the least is "GCG" (see Table 1 below). Codon usage for various organisms and organelles can be found at the website http://www.kazusa.or.jp/codon/, incorporated herein by reference, allowing one of skill in the art to optimize codon usage for expression in various organisms using the disclosures herein. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria or chloroplasts, based on the preferred codon usage as would be known to those of ordinary skill in the art.

TABLE 1

Preferred Human DNA Codons

| Amino Acids | | | Codons | | | | | |
|---|---|---|---|---|---|---|---|---|
| Alanine | Ala | A | GCC | GCT | GCA | GCG | | |
| Cysteine | Cys | C | TGC | TGT | | | | |
| Aspartic acid | Asp | D | GAC | GAT | | | | |
| Glutamic acid | Glu | E | GAG | GAA | | | | |
| Phenylalanine | Phe | F | TTC | TTT | | | | |
| Glycine | Gly | G | GGC | GGG | GGA | GGT | | |
| Histidine | His | H | CAC | CAT | | | | |
| Isoleucine | Ile | I | ATC | ATT | ATA | | | |
| Lysine | Lys | K | AAG | AAA | | | | |
| Leucine | Leu | L | CTG | CTC | TTG | CTT | CTA | TTA |
| Methionine | Met | M | ATG | | | | | |
| Asparagine | Asn | N | AAC | AAT | | | | |
| Proline | Pro | P | CCC | CCT | CCA | CCG | | |
| Glutamine | Gln | Q | CAG | CAA | | | | |
| Arginine | Arg | R | CGC | AGG | CGG | AGA | CGA | CGT |
| Serine | Ser | S | AGC | TCC | TCT | AGT | TCA | TCG |
| Threonine | Thr | T | ACC | ACA | ACT | ACG | | |
| Valine | Val | V | GTG | GTC | GTT | GTA | | |
| Tryptophan | Trp | W | TGG | | | | | |
| Tyrosine | Tyr | Y | TAC | TAT | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferrably about 81% and about 90%; or even more preferably, between about 91% and about 99%; of nucleotides that are identical to the nucleotides of SEQ ID NO:1 or NO:3 will be sequences that are "essentially as set forth in SEQ ID NO:1 or NO:3."

B. Nucleic Acid Hybidization

The nucleic acid sequences disclosed herein also have a variety of uses, such as for example, utility as probes or primers in nucleic acid hybridization embodiments.

Naturally, the present invention also encompasses DNA segments that are complementary, or essentially complementary, to the sequence set forth in SEQ ID NO:1 and NO:3. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 and NO:3 under stringent conditions such as those described herein.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suite a particular application. For example, in other embodiments, hybridization may be achieved under conditions of, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1 or NO:3, such as, for example, about 8, about 10 to about 14, or about 15 to about 20 nucleotides, and that are chromosome sized pieces, up to about 1,000,000, about 750,000, about 500,000, about 250,000, about 100,000, about 50,000, about 20,000, or about 10,000, or about 5,000 base pairs in length, with segments of about 3,000 being preferred in certain cases, as well as DNA segments with total lengths of about 1,000, about 500, about 200, about 100 and about 50 base pairs in length (including all intermediate lengths of these lengths listed above, i.e., any range derivable therein and any integer derivable therein such a range) are also contemplated to be useful.

For example, it will be readily understood that "intermediate lengths", in these contexts, means any length between the quoted ranges, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 105, 110, 115, 120, 130, 140, 150, 160, 170, 180, 190, including all integers through the 200-500; 500-1,000; 1,000-2,000;

2,000-3,000; 3,000-5,000; 5,000-10,000 ranges, up to and including sequences of about 12,001, 12,002, 13,001, 13,002, 15,000, 20,000 and the like.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid (SEQ ID NO:1 and NO:3) segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1-2 kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the "G+C" content, type of target nucleic acid, source of nucleic acid, size of hybridization probe, etc.). Following washing of the hybridized surface to remove non-specifically bound probe molecules, hybridization is detected, or even quantified, by means of the label.

C. Nucleic Acid Amplification

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to NGVN genes are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EP 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one=sided PCR" (Frohman, 1990, incorporated herein by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

D. Nucleic Acid Detection

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols (See Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods for genetic screening to accurately detect mutations in genomic DNA, cDNA or RNA samples may be employed, depending on the specific situation.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see above) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an E. coli enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

E. Cloning of Additional NGVN Genes

The present invention contemplates cloning NGVN genes or cDNAs from animal (e.g., mammalian) organisms. A technique often employed by those skilled in the art of protein production today is to obtain a so-called "recombinant" version of the protein, to express it in a recombinant cell and to obtain the protein, polypeptide or peptide from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library. The screening protocol may utilize nucleotide segments or probes derived from SEQ ID NOS:1 or 3. Additionally, antibodies designed to bind to the expressed NGVN proteins, polypeptides, or peptides may be used as probes to screen an appropriate mammalian DNA expression library. Alternatively, activity assays may be employed. The operation of such screening protocols are well known to those of skill in the art and are described in detail in the scientific literature, for example, in Sambrook et al. (1989), incorporated herein by reference. Moreover, as the present invention encompasses the cloning of genomic segments as well as cDNA molecules, it is contemplated that suitable genomic cloning methods, as known to those in the art, may also be used.

As used herein "designed to hybridize" means a sequence selected for its likely ability to hybridize to a mammalian NGVN gene, for example due to the expected high degree of homology between the human, rat, or mouse NGVN gene and the NGVN genes from other mammals. Also included are segments or probes altered to enhance their ability to hybridize to or bind to a mammalian NGVN gene. Additionally, these regions of homology also include amino acid sequences of 4 or more consecutive amino acids selected and/or altered to increase conservation of the amino acid sequences in comparison to the same or similar region of residues in the same or related genes in one or more species. Such amino acid sequences may derived from amino acid sequences encoded by the NGVN gene, and more particularly from the isolated sequences of SEQ ID NO:2.

Designing probe sequences may involve selection of regions of highly conserved nucleotide sequences between various species for a particular gene or related genes, relative to the general conservation of nucleotides of the gene or related genes in one or more species. Comparison of the amino acid sequences conserved between one or more species for a particular gene may also be used to determine a group of 4 or more consecutive amino acids that are conserved relative to the protein encoded by the gene or related genes. The nucleotide probe or primers may then be designed from the region of the gene that encodes the conserved sequence of amino acids.

One may also prepare fusion proteins, polypeptides and peptides, e.g., where the NGVN proteinaceous material coding regions are aligned within the same expression unit with other proteins, polypeptides or peptides having desired functions, such as for purification or immunodetection purposes (e.g., proteinaceous compostions that may be purified by affinity chromatography and enzyme label coding regions, respectively).

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2 and also larger polypeptides up to and including proteins corresponding to the full-length sequences set forth in SEQ ID NO:2, and any range derivable therein and any integer derivable therein such a range.

In addition to the "standard" DNA and RNA nucleotide bases, modified bases are also contemplated for use in particular applications of the present invention. A table of exemplary, but not limiting, modified bases is provided herein below.

TABLE 2

Modified Bases

| Abbr. | Modified base description |
|---|---|
| ac4c | 4-acetylcytidine |
| chm5u | 5-(carboxyhydroxylmethyl)uridine |
| Cm | 2'-O-methylcytidine |
| Cmnm5s2u | 5-carboxymethylaminomethyl-2-thioridine |
| Cmnm5u | 5-carboxymethylaminomethyluridine |
| D | Dihydrouridine |
| Fm | 2'-O-methylpseudouridine |
| gal q | Beta,D-galactosylqueosine |
| Gm | 2'-O-methylguanosine |
| I | Inosine |
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |
| Mam5s2u | 5-methoxyaminomethyl-2-thiouridine |
| Man q | Beta,D-mannosylqueosine |
| Mcm5s2u | 5-methoxycarbonylmethyl-2-thiouridine |
| Mcm5u | 5-methoxycarbonylmethyluridine |
| Mo5u | 5-methoxyuridine |
| Ms2i6a | 2-methylthio-N6-isopentenyladenosine |
| Ms2t6a | N-((9-beta-D-ribofuranosyl-2-methylthiopurine-6-yl)carbamoyl)threonine |
| Mt6a | N-((9-beta-D-ribofuranosylpurine-6-yl)N-methyl-carbamoyl)threonine |
| Mv | Uridine-5-oxyacetic acid methylester |
| o5u | Uridine-5-oxyacetic acid (v) |
| Osyw | Wybutoxosine |
| P | Pseudouridine |
| Q | Queosine |
| s2c | 2-thiocytidine |
| s2t | 5-methyl-2-thiouridine |
| s2u | 2-thiouridine |
| s4u | 4-thiouridine |
| T | 5-methyluridine |
| t6a | N-((9-beta-D-ribofuranosylpurine-6-yl)carbamoyl)threonine |
| Tm | 2'-O-methyl-5-methyluridine |
| Um | 2'-O-methyluridine |
| Yw | Wybutosine |
| X | 3-(3-amino-3-carboxypropyl)uridine,(acp3)u |

F. Mutagenesis, Peptidomimetics and Rational Drug Design

It will also be understood that this invention is not limited to the particular nucleic acid and amino acid sequences of SEQ ID NO:2. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins, polypeptides or peptides that have variant amino acids sequences.

The DNA segments of the present invention encompass biologically functional equivalent NGVN proteins, polypeptides, and peptides. Such sequences may arise as a consequence of codon redundancy and functional equivalency that are known to occur naturally within nucleic acid sequences and the proteinaceous compositions thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes may be introduced, for example, through the application of site-directed mutagenesis techniques as discussed herein below, e.g., to introduce improvements to the antigenicity of the proteinaceous composition or to test mutants in order to examine NGVN activity at the molecular level.

Site-specific mutagenesis is a technique useful in the preparation of individual peptides, or biologically functional equivalent proteins, polypeptides or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired proteinaceous molecule. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

As modifications and changes may be made in the structure of the NGVN genes, nucleic acids (e.g., nucleic acid segments) and proteinaceous molecules of the present invention, and still obtain molecules having like or otherwise desirable characteristics, such biologically functional equivalents are also encompassed within the present invention.

For example, certain amino acids may be substituted for other amino acids in a proteinaceous structure without appreciable loss of interactive binding capacity with structures such as, for example, antigen-binding regions of antibodies, binding sites on substrate molecules or receptors, or such like. Since it is the interactive capacity and nature of a proteinaceous molecule that defines that proteinaceous molecule's biological functional activity, certain amino acid sequence substitutions can be made in a proteinaceous molecule sequence (or, of course, its underlying DNA coding sequence) and nevertheless obtain a proteinaceous molecule with like (agonistic) properties. It is thus contemplated that various changes may be made in the sequence of NGVN proteins, polypeptides or peptides, or the underlying nucleic acids, without appreciable loss of their biological utility or activity.

Equally, the same considerations may be employed to create a protein, polypeptide or peptide with countervailing, e.g., antagonistic properties. This is relevant to the present invention in which NGVN mutants or analogues may be generated. For example, a NGVN mutant may be generated and tested for NGVN activity to identify those residues important for NGVN activity. NGVN mutants may also be synthesized to reflect a NGVN mutant that occurs in the human population and that is linked to the development of cancer. Such mutant proteinaceous molecules are particularly contemplated for use in generating mutant-specific antibodies and such mutant DNA segments may be used as mutant-specific probes and primers.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein above for use in such embodiments, as well as for other uses, such as in the design of probes and primers and the like.

In terms of functional equivalents, it is well understood by the skilled artisan that, inherent in the definition of a "biologically functional equivalent" protein, polypeptide, peptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, where shorter length peptides are concerned, it is contemplated that fewer amino acids changes should be made within the given peptide. Longer domains may have an intermediate number of changes. The full length protein will have the most tolerance for a larger number of changes. Of course, a plurality of distinct proteins/polypeptide/peptides with different substitutions may easily be made and used in accordance with the invention.

It is also well understood that where certain residues are shown to be particularly important to the biological or structural properties of a protein, polypeptide or peptide, e.g., residues in binding regions or active sites, such residues may not generally be exchanged. In this manner, functional equivalents are defined herein as those peptides which maintain a substantial amount of their native biological activity.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a proteinaceous molecule is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein, polypeptide or peptide thereby created is intended for use in immunological embodiments, as in certain embodiments of the present invention. U.S. Pat. No. 4,554, 101, incorporated herein by reference, states that the greatest local average hydrophilicity of a proteinaceous molecule, as governed by the hydrophilicity of its adjacent amino acids, correlates with its immunogenicity and antigenicity, i.e., with a biological property of the proteinaceous molecule.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

In addition to the NGVN peptidyl compounds described herein, it is contemplated that other sterically similar compounds may be formulated to mimic the key portions of the peptide structure. Such compounds, which may be termed peptidomimetics, may be used in the same manner as the peptides of the invention and hence are also functional equivalents.

Certain mimetics that mimic elements of proteinaceous molecules secondary structure are described in Johnson et al. (1993). The underlying rationale behind the use of peptide mimetics is that the peptide backbone of proteinaceous molecules exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of β-turns within proteinaceous molecules, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds NGVN can be designed and then synthesized. It will be understood that all such sterically designed constructs fall within the scope of the present invention.

In addition to the 20 "standard" amino acids provided through the genetic code, modified or unusual amino acids are also contemplated for use in the present invention. A table of exemplary, but not limiting, modified or unusual amino acids is provided herein below.

TABLE 3

Modified and Unusual Amino Acids

| Abbr. | Amino Acid |
|---|---|
| Aad | 2-Aminoadipic acid |
| Baad | 3-Aminoadipic acid |
| Bala | Beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| aHyl | Allo-Hydroxylysine |
| 3Hyp | 3-Hydroxyproline |
| 4Hyp | 4-Hydroxyproline |
| Ide | Isodesmosine |
| aIle | Allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

In one aspect, an compound may be designed by rational drug design to function as a NGVN in inhibition serine proteases. The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for the NGVN protein of the invention or a fragment thereof. This could be accomplished by X-ray crystallography, computer modeling or by a combination of both approaches. An alternative approach, involves the random replacement of functional groups throughout the NGVN protein, polypeptides or peptides, and the resulting affect on function determined.

It also is possible to isolate a NGVN protein, polypeptide or peptide specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have enhanced and improved biological activity, for example, serine protease or tumor growth or metastasis inhibition, relative to a starting NGVN proteinaceous sequences. By virtue of the ability to recombinantly produce sufficient amounts of the NGVN proteins, polypeptides or peptides, crystallographic studies may be preformed to determine the most likely sites for mutagenesis and chemical mimicry. In addition, knowledge of the chemical characteristics of these compounds permits computer employed predictions of structure-function relationships. Computer models of various polypeptide and peptide structures are also available in the literature or computer databases. In a non-limiting example, the Entrez database (http://www.ncbi.nlm.nih.gov/Entrez/) may be used by one of ordinary skill in the art to identify target sequences and regions for mutagenesis.

3. Diagnosing BBS and Related Conditions

As discussed above, the present inventors have determined that alterations in the NGVN gene are associated with BBS. Therefore, NGVN and the corresponding gene may be employed as a diagnostic or prognostic indicator of BBS in general, and of related disorders such as diabetes, hypertension, retinal degeneration, renal carcinoma, renal malformation, congenital heart defects, limb deformity and obesity. More specifically, point mutations, deletions, insertions or regulatory perturbations relating to NGVN will be identified. The present invention contemplates further the diagnosis of disease states by detecting changes in the levels of NGVN expression.

A. Genetic Diagnosis

One embodiment of the instant invention comprises a method for detecting variation in the expression of NGVN. This may comprise determining the level of NGVN expressed, or determining specific alterations in the expressed product. Obviously, this sort of assay has importance in the diagnosis of related BBS, but it also is relevant to other disease states such as diabetes, retinal degeneration, renal carcinoma (cancers), renal malformation, congenital heart defects, limb deformity, hypertension and obesity.

The biological sample can be any tissue or fluid. Various embodiments include cells of the skin, muscle, fascia, brain, prostate, breast, endometrium, lung, head & neck, pancreas, small intestine, blood cells, liver, testes, ovaries, colon, rectum, skin, stomach, esophagus, spleen, lymph nodes, bone marrow or kidney. Other embodiments include fluid samples such as peripheral blood, lymph fluid, ascites, serous fluid, pleural effusion, sputum, cerebrospinal fluid, lacrimal fluid, stool urine or amniotic fluid.

Nucleic acids used are isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have BBS or BBS-related pathologies. In this way, it is possible to correlate the amount or kind of BBS detected with various clinical states.

Various types of defects have been identified by the present inventors. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of NGVN produced, both by altering the transcription of the gene or in destabilizing or otherwise altering the processing of either the transcript (mRNA) or protein.

The following table provides a summary of the changes identified in the NGVN gene:

TABLE 4

| Exon # | DNA Change (cDNA base) | Protein Change |
|---|---|---|
| 02 | T224G | Val75Gly |
| 08 | C814T | Arg272Stop |
| 08 | C823T | Arg275Stop |
| 08 | 940delA | Frameshift |
| 10 | 1206insA | Frameshift |
| 03 | A367G | Ile123Val |
| 12 | A1413C | Val471Val |

It is contemplated that other mutations in the NGVN gene may be identified in accordance with the present invention by detecting a nucleotide change in particular nucleic acids (U.S. Pat. No. 4,988,617, incorporated herein by reference). A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO, e.g., U.S. Pat. No. 5,639,611), dot blot analysis, denaturing gradient gel electrophoresis (e.g., U.S. Pat. No. 5,190,856 incorporated herein by reference), RFLP (e.g., U.S. Pat. No. 5,324,631 incorporated herein by reference) and PCR™-SSCP. Methods for detecting and quantitating gene sequences, such as mutated genes and oncogenes, in for example biological fluids are described in U.S. Pat. No. 5,496,699, incorporated herein by reference.

a. Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemillumiscent (luciferase).

b. Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990, Polymerase chain reaction methodologies are well known in the art.

Another method for amplification is the ligase chain reaction ("LCR" U.S. Pat. Nos. 5,494,810, 5,484,699, EP 320 308, each incorporated herein by reference). In LCR, two complementary probe pairs are prepared, and in the presence of the target sequence, each pair will bind to opposite complementary strands of the target such that they about. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase an RNA-directed RNA polymerase, also may be used as still another amplification method in the present invention. In this method, a replicative sequence of RNA that has a region complementary to that of a target is added to a sample in the presence of an RNA polymerase. The polymerase will copy the replicative sequence that can then be detected. Similar methods also are described in U.S. Pat. No. 4,786,600, incorporated herein by reference, which concerns recombinant RNA molecules capable of serving as a template for the synthesis of complementary single-stranded molecules by RNA-directed RNA polymerase. The product molecules so formed also are capable of serving as a template for the synthesis of additional copies of the original recombinant RNA molecule.

An isothermal amplification method, in which restriction endonucleases and ligases are used to achieve the amplification of target molecules that contain nucleotide 5'-[alpha-thio]-triphosphates in one strand of a restriction site also may be useful in the amplification of nucleic acids in the present invention (Walker et al., 1992; U.S. Pat. No. 5,270,184, incorporated herein by reference). U.S. Pat. No. 5,747,255 (incorporated herein by reference) describes an isothermal amplification using cleavable oligonucleotides for polynucleotide detection. In the method described therein, separated populations of oligonucleotides are provided that contain complementary sequences to one another and that contain at least one scissile linkage which is cleaved whenever a perfectly matched duplex is formed containing the linkage. When a target polynucleotide contacts a first oligonucleotide cleavage occurs and a first fragment is produced which can hybridize with a second oligonucleotide. Upon such hybridization, the second oligonucleotide is cleaved releasing a second fragment that can, in turn, hybridize with a first oligonucleotide in a manner similar to that of the target polynucleotide.

Strand Displacement Amplification (SDA) is another method of carrying out isothermal amplification of nucleic acids which involves multiple rounds of strand displacement and synthesis, i.e., nick translation (e.g., U.S. Pat. Nos. 5,744,311; 5,733,752; 5,733,733; 5,712,124). A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EP 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, also may be used in the amplification step of the present invention. Wu et al., (1989), incorporated herein by reference in its entirety.

c. Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

d. Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods (See Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

e. Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al., 1994). The present invention provides methods by which any or all of these types of analyses may be used. Using the sequences disclosed herein, oligonucleotide primers may be designed to permit the amplification of sequences throughout the NGVN gene that may then be analyzed by direct sequencing.

f. Kit Components

All the essential materials and reagents required for detecting and sequencing NGVN and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

g. Design and Theoretical Considerations for Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR™ products and the relative mRNA abundances is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundances of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the experiments described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5-100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

h. Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Immunodiagnosis

Antibodies can be used in characterizing the NGVN content of healthy and diseased tissues, through techniques such as ELISAs and Western blotting. This may provide a prenatal screen or in counseling for those individuals seeking to have children.

The use of antibodies of the present invention, in an ELISA assay is contemplated. For example, anti-NGVN antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for NGVN that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The steps of various other useful immunodetection methods have been described in the scientific literature, such as, e.g., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

4. Methods for Screening Active Compounds

The present invention also contemplates the use of NGVN and active fragments, and nucleic acids coding therefor, in the screening of compounds for activity in either stimulating NGVN activity, overcoming the lack of NGVN or blocking the effect of a mutant NGVN molecule. These assays may make use of a variety of different formats and may depend on the kind of "activity" for which the screen is being conducted.

A. In Vitro Assays

In one embodiment, the invention is to be applied for the screening of compounds that bind to the NGVN polypeptide or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of NGVN to a natural or artificial substrate or binding partner. Competitive binding assays can be performed in which one of the agents (NGVN, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with NGVN and washed. Bound polypeptide is detected by various methods.

Purified NGVN can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the NGVN active region to a solid phase.

Various cell lines containing wild-type or natural or engineered mutations in NGVN gene can be used to study various functional attributes of NGVN and how a candidate compound affects these attributes. Methods for engineering mutations are described elsewhere in this document, as are naturally-occurring mutations in NGVN that lead to, contribute to and/or otherwise cause BBS. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of NGVN, or related pathways, may be explored.

B. In Vivo Assays

The present invention also encompasses the use of various animal models. Thus, any identity seen between human and other animal NGVN provides an excellent opportunity to examine the function of NGVN in a whole animal system where it is normally expressed. By developing or isolating mutant cells lines that fail to express normal NGVN, one can generate models in mice that will be highly predictive of BBS and related syndromes in humans and other mammals.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

C. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for NGVN or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a NGVN-specific antibody, selected by a functional assay, and then solve its crystal structure. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved NGVN activity or which act as stimulators, inhibitors, agonists, antagonists of NGVN or molecules affected by NGVN function. By virtue of the availability of cloned NGVN gene sequences, sufficient amounts of NGVN can be produced to perform crystallographic studies. In addition, knowledge of the polypeptide sequences permits computer employed predictions of structure-function relationships.

D. Transgenic Animals/Knockout Animals

In one embodiment of the invention, transgenic animals are produced which contain a functional transgene encoding a functional NGVN polypeptide or variants thereof. Transgenic animals expressing NGVN transgenes, recombinant cell lines derived from such animals and transgenic embryos may be useful in methods for screening for and identifying agents that induce or repress function of NGVN. Transgenic animals of the present invention also can be used as models for studying disease states.

In one embodiment of the invention, a NGVN transgene is introduced into a non-human host to produce a transgenic animal expressing a human or murine NGVN gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous NGVN by homologous recombination between the transgene and the endogenous gene; or the endogenous gene may be eliminated by deletion as in the preparation of "knock-out" animals. Typically, a NGVN gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress NGVN or express a mutant form of the polypeptide. Alternatively, the absence of a NGVN in "knock-out" mice permits the study of the effects that loss of NGVN protein has on a cell in vivo. Knock-out mice also provide a model for the development of NGVN-related disease.

As noted above, transgenic animals and cell lines derived from such animals may find use in certain testing experiments. In this regard, transgenic animals and cell lines capable of expressing wild-type or mutant NGVN may be exposed to test substances. These test substances can be screened for the ability to enhance wild-type NGVN expression and or function or impair the expression or function of mutant NGVN.

5. Methods for Treating BBS

The present invention also contemplates the treatment of BBS and related symptoms such as obesity, diabetes, renal cancer or other abnormalities, retinal degeneration and hypertension by providing a NGVN protein to cells of an affected individual.

A. Genetic Based Therapies

Specifically, the present inventors intend to provide, to a cell, an expression construct capable of providing NGVN to that cell. Because the sequence homology between the human, and other NGVN, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus; vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

B. Protein Therapy

Another therapy approach is the provision, to a subject, of NGVN polypeptide, active fragments, syn that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 5).

TABLE 5

Tissue specific promoters

| Tissue | Promoter |
| --- | --- |
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |

TABLE 5-continued

Tissue specific promoters

| Tissue | Promoter |
| --- | --- |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bicistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters should not be construed to be exhaustive or limiting, those of skill in the art will know of other promoters that may be used in conjunction with the promoters and methods disclosed herein.

b. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 6 and Table 7). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

c. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

TABLE 6

ENHANCER

Immunoglobulin Heavy Chain
Immunoglobulin Light Chain
T-Cell Receptor
HLA DQ α and DQ β
β-Interferon
Interleukin-2
Interleukin-2 Receptor

TABLE 6-continued

ENHANCER

MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 7

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), H$_2$O$_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

7. Methods of Gene Transfer

In order to mediate the effect transgene expression in a cell, it will be necessary to transfer the therapeutic expression constructs of the present invention into a cell. Such transfer may employ viral or non-viral methods of gene transfer. This section provides a discussion of methods and compositions of gene transfer.

A. Viral Vector-Mediated Transfer

In certain embodiments, the NGVN gene is incorporated into a viral particle to mediate gene transfer to a cell. Typically, the virus simply will be exposed to the appropriate host cell under physiologic conditions, permitting uptake of the virus. The present methods may be advantageously employed using a variety of viral vectors, as discussed below.

a. Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (EIA) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

b. Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

c. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al, 1997; Mizukami et al., 1996).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

d. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) canary pox virus, and herpes viruses may be employed. These viruses offer several features for use in gene transfer into various mammalian cells.

B. Non-Viral Transfer

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also may be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

8. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should lye suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

9. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patients and Families

Patients were identified through the Department of Opthalmology at the University of Iowa or by collaborating investigators at other institutions. Signed, informed consent was obtained from each patient prior to the collection of a sample of whole blood (5 to 10 ml) using protocols approved by the Institutional Review Board at the University of Iowa.

DNA Isolation

Genomic DNA was isolated from whole blood according to methods that have been published previously. YAC DNA was isolated using the DNA-Pure yeast genomic kit (CPG, Inc.). BAC DNA was prepared via an alkaline lysis protocol as implemented in the Wizard Plus Miniprep Kit (Promega) with the following modification to the protocol. Instead of loading the supernatant onto a vacuum column, it was precipitated with a 2× volume of absolute EtOH. In addition, 150 µl volumes were used for the commercial solutions in place of the 200 µl volumes suggested in the protocol. The precipitated DNA was then washed with 70% EtOH and dried. The DNA pellet was then resuspended in 50 µl of ddH$_2$O. Finally, plasmid DNA was prepared using a Wizard Plus Miniprep kit (Promega) following the recommended protocol. Culture sizes for DNA preparation from YACs, BACs and plasmids were 1.5 ml of the appropriate media and antibiotics for each construct.

Marker Typing

PCR amplification for the analysis of short tandem repeat polymorphisms (STRPs) was performed using 20 ng of genomic DNA in 5 µl reactions containing 0.5 µl of 10×PCR buffer [100 mM Tris-HCl (pH 8.8), 500 mM KCl, 15 mM MgCl$_2$, 0.01% gelatin (w/v)], 200 µM each of dATP, dCTP, dGTP and dTTP, 2.5 µmol of each primer and 0.2 units of Taq polymerase (BMB, ISC). Samples were subjected to 35 cycles of 94° C. for 30 sec, (50, 52, 55 or 57° C. as required) for 30 sec and 72° C. for 30 sec. Amplification products were electrophoresed on 6% polyacrylamide gels containing 7.7 M urea at 60 W for approximately 2 h. The bands were detected by silver staining. Bassam (1991).

Marker typing for physical mapping was performed on 2% agarose gels using a PCR reaction size of 10 µl. Reaction conditions were as described above with the following exceptions. For markers that proved difficult to amplify using the standard Taq polymerase, the inventors substituted an equal amount of AmpliTaq (ABI) along with an initial incubation of the PCR mixture at 94° C. for 10 minutes. For PCR reactions involving YAC, BAC or plasmid DNA, 1 to 2 ng of DNA was utilized as template. For colony PCR, a small number of cells were inoculated into 20 µl of ddH$_2$O. One µl of this suspension was used as template for the PCR reaction.

Oligonucleotide primers for the STRPs were obtained as MapPairs (Research Genetics or Integrated DNA Technologies). The custom primers required for this study were designed using the PRIMER 0.5 program and synthesized commercially (Research Genetics). Size standards for the 2% agarose gels were 100 bp ladder (Gibco/BRL) and for the denaturing acrylamide gels a 50 bp ladder (Gibco/BRL). For the 0.8% agarose gels, lambda DNA digested with StyI was used as a size marker.

YAC, BAC and cDNA Identification

Initially, YACs were identified by searching a database at the Whitehead Institute/MIT Genome Center (http://www-genome.wi.mit.edu) (Hudson et al., 1995) with STSs known to be in the 16q21 region. Subsequently, YACs and BACs were identified by a PCR-based screening assay of pooled libraries (Research Genetics) using various STSs within each region. ESTs were identified by a BLASTN search of the public dbEST database available through a web interface NCBI. Altschul & Lipman (1990).

Gene Identification and Characterization

Raw SCF files from ABI 373A and 377 sequencers were imported directly into the Sequencher v3.1 program (GeneCodes). Contigs were generated by comparing all fragments in a project with the parameters of at least a 50 bp overlap in sequence with a 80% level of homology. Genomic sequence of BACs from the 16q21 region was submitted to the BLAST server at NCBI for a BLASTN analysis on both the NR and dbEST databases. Altschul & Lipman (1990). Any region which gave a significant score ($p<10^{-5}$) was also submitted for a BLASTX screen of the SWISS-PROT database. EST sequence was obtained from GENBANK and SCF files from the WashU-Merck ftp site (ftp://genome.wustl.edu).

Sequencing Plasmids and PCR Products

PCR products for sequencing were amplified in a 50 µl reaction size and purified using the Quiaquick PCR Clean-up kit (Promega). 500 ng of plasmid DNA (in 4.5 µl) or 4.5 µl of purified PCR product was used as template for a sequencing reaction. One µl of primer (20 pmoles) and 4.5 µl of terminator sequencing mix (Amersham) was added for a final reaction size of 10 µl. Cycling conditions were performed as specified by the manufacturer. The sequencing reactions were precipitated in the presence of linear acrylamide and resuspended in 2 µl of loading buffer. The reactions were analyzed on an ABI 377 using a run time of 3 h.

Mutation Detection and Confirmation

Mutation detection was performed using single strand conformation polymorphism (SSCP) analysis and direct sequencing of PCR products. PCR products were electrophoresed on SSCP gels (5 ml glycerol, 5 ml 5×TBE, 12.5 ml 37.5:1 acrylamide/bis and 77.5 ml ddH$_2$O) for 3 to 4 hr in 0.25×TBE at room temperature. Gels were silver stained as described above. Abnormal variants were sequenced and compared to a control sample to detect any changes from that of the normal sequence. Mutations were confirmed by amplification-refractory mutation system (ARMS) analysis. Newton (1989).

Northern Blot Analysis

Human Multiple Tissue Northern (MTN) blots I and III and Human Fetal MTN Blot II were obtained from Clontech (San Francisco, Calif.). The blots were hybridized with a 300 bp DNA probe derived from the 3' UIR of the human NGVN gene. The probe was amplified by PCR using the NGVN-forward (5'-AATAACCTTGGTGAGTTGTAC-3') and NGVN-reverse (5'-ATACAAATGGGCAATTCTGAT-3') primers. The probe was labeled with $^{32}$P-dCTP using Ready-To-Go DNA Labeling Beads (Amersham Pharmacia Biotech, Piscataway, N.J.). Hybridization and autoradiography were performed as described previously. The blots were stripped of radioactivity and re-hybridized with a cDNA probe for β-actin (Clontech, San Francisco, Calif.) to assess equal loading of the RNA.

Example 2

Results

Clinical Data

The clinical features of the large Bedouin kindred (pedigree 1) have previously been described. Briefly, all of the cardinal features of BBS were present in at least some of the members of this family. None of the patients had spastic paraplegia, colobomas or deafness, diagnostic features of Laurence-Moon, Biemond and Alstrom syndromes, respectively. Pedigree 2 consisted of four affected individuals of Kurdish ancestry, all of which had at least three of the cardinal features of BBS syndrome. Within the two families there was a clear dichotomy between affected and unaffected individuals in that none of the unaffected individuals had any of the features of Bardet-Biedl syndrome.

Affected individual from both families had very similar distributions of polydactyly, usually affecting both upper and lower extremities. All but one patient had polydactyly affecting at least three limbs, and the exception had two limb polydactyly. Obesity was more apparent in kindred 2 compared to kindred 1. Hypogenitalism was apparent in male members of both families. Two patients in family 1 had unilateral renal hypoplasia. Retinal degeneration was a striking feature of the disorder in both families. All affected probands used in this study had at least three of the cardinal features of BBS. The minimal criteria for inclusion in the study were the diagnostic features of obesity, polydactyl), and pigmented retinopathy.

Definition of Critical Interval by Genetic Analysis

In 1993, linkage studies and haplotype analysis of a large inbred Bedouin kindred mapped the BBS2 locus to an 18 cM region within 16q21 flanked by the markers D16S419 and D16S265. Analysis of additional genetic markers within this region allowed the critical interval to be narrowed to approximately 6 cM. This proved to be the best estimate of the critical interval that was possible based upon the genetic information provided by the affected individuals in this family. As BBS is a highly penetrant disorder, it was decided that the study of unaffected individuals within the pedigree might allow for the further refinement of the critical interval with a high level of confidence in the results.

One of the unaffected individuals from the Bedouin pedigree was found to have a recombination event at the distal end of the critical interval that narrowed the distal flank to a region within the BAC RP_11-152E5. However, no additional refinement was possible for the proximal flanking region using information from unaffected individuals from the pedigree. Over 40 additional DNA samples were obtained from unaffected members of the Bedouin tribe that was segregating the BBS2 locus in an attempt to further refine the critical interval. Given the high penetrance of BBS, the detection of a region containing homozygosity for the affected haplotype in an unaffected individual would strongly suggest that the BBS2 gene would be excluded from the region. Analysis of these additional samples yielded an unaffected individual who had inherited the affected haplotype in the homozygous state at the proximal end of the critical region. This allowed the inventors to exclude the BBS2 gene from a region that was proximal to D16S408. The refined critical interval included an approximately 2 cM region between the markers D16S408 and 152e5-CA.

Physical Mapping

To facilitate the cloning and characterization of the BBS2 gene, the inventors constructed a physical map of the critical interval. An initial physical map that was based on YAC clones allowed for low resolution localization of genetic markers and candidate genes within the critical interval. Once the genetic interval was refined to the smallest size possible, the physical map was converted to one that was based on BAC clones. The smaller size of the BAC clones allowed for higher resolution mapping of genetic markers and candidate genes within the interval. Radiation hybrid mapping using the Stanford G3 mapping panel was used to confirm the order obtained from the BAC-based physical maps as well as to anchor this region within the Stanford chromosome 16 G3 radiation hybrid map.

Candidate Gene Identification

The BAC-based physical map was used to select a subset of BACs for sample sequencing at 1× coverage. The sequence information obtained from sample sequencing was combined with that available from the public sequence databases and used for the identification of candidate genes for BBS2. BLASTN analysis was performed against the nr and dbEST databases that are maintained by NCBI. This allowed the inventors to identify a number of unique genes and Unigene EST clusters. Over 30 unique genes or EST clusters were identified, not including the multiple metallothionein genes that are known to map within the region. The genes were prioritized for mutation screening based on criteria including (i) availability of known cDNA and/or genomic sequence, (ii) known expression pattern of the gene consistent with the BBS phenotype and (iii) the availability of any functional information. Although the use of information from unaffected individuals to narrow the critical interval was postulated to be reliable, an attractive candidate gene that mapped within the more conservative interval defined by an "affected-only" analysis was not strictly ruled out, but deemed to be of lower priority for analysis.

Mutation Screening of Candidate Genes

A second inbred pedigree consisting of 4 affected individuals was also found to be linked to the BBS2 locus. Genotyping of DNA from the three affected individuals from whom DNA was available for demonstrated that all were homozygous for the same haplotype. This haplotype was not found in the homozygous state in any of the unaffected individuals in the family. The affected haplotype was found to be different than that segregating within the large inbred Bedouin family suggesting that the mutation in each family would likely be different.

The availability of two inbred BBS2 pedigrees with likely independent mutations allowed the inventors to conduct a sequencing-based mutation screen of BBS2 candidate genes. PCR amplicons that covered the coding sequence and consensus splice sites for each candidate gene were amplified from genomic DNA from an affected individual from each of the two BBS2 pedigrees, and the amplification products were directly sequenced. The DNA sequence generated from the two samples were compared with each other as well as to sequence available in the public DNA sequence databases. Fifteen candidate genes were screened without finding any evidence for pathological variants.

NGVN Gene Structure and Expression Profile

UniGene EST cluster Hs.24809 was selected for analysis based on the suggestion a of a broad expression pattern and on map position within the narrowest candidate interval. The UniGene cluster contained 194 ESTs as well as 6 mRNA sequences. When these sequences were assembled into contigs, two distinct, unique contigs were created. Both contigs were found to map to the same BAC (RP_11-5A3) that was located within the BBS2 critical interval on chromosome 16.

One of the contigs was found to contain an open reading frame of 1461 bp. Partial gene structure could be determined for this genes which yielded 9 exons for analysis. The second contig was found to contain an open reading frame of 2,163 bp. The complete gene structure was ascertained for this gene, now referred to as negevin (NGVN). Comparison of cDNA sequence with genomic sequence revealed a total of 17 exons. Both genes were screened for mutations. While the mutation screen of the first gene produced no evidence of pathologically significant variants, a number of mutations were detected in the NGVN gene.

NGVN was amplified from a human fetal cDNA library and sequenced to confirm the cDNA sequence that was predicted from the EST contig. Sixty-six of the 193 ESTs from UniGene cluster Hs.24809 were assigned to the NGVN contig. The tissue distribution of these ESTs suggested that NGVN was a widely expressed gene. Northern blot analysis confirmed the broad expression pattern of NGVN and revealed a NGVN mRNA size estimate of approximately 3.0 kb. This size estimate agrees well with the size predicted from the genomic DNA sequence. A minor Northern blot band of smaller molecular weight was apparent in trachea tissue, suggesting alternative splicing.

NGVN Mutations

Mutation screening of NGVN produced strong mutation candidates in both of the linked BBS2 families that were part of the initial mutation screen. The smaller BBS2-linked family was found to harbor a 1 bp deletion in exon 8 (940delA). The mutation was found in the homozygous state in all three of the affected individuals, and was not found in the homozygous state in unaffected family members. The frameshift has not been detected to date in any other family or proband that has been examined, or in 96 control individuals.

Two sequence variants were detected in the large, inbred Bedouin BBS family. An A to G transition at nucleotide position 367 (Ile123Val) was detected in exon 3. Ile123Val is conservative and thus was not judged to be responsible for the BBS phenotype in the family. A second variant, a T to G transversion, was found at nucleotide position 224 (Val75Gly) in exon 2 that produced a non-conservative amino acid change. This variant is postulated to be the disease causing mutation in this family. Both DNA sequence variants segregate with the BBS phenotype within the family in that all affected individuals were homozygous for the sequence variant, all obligate carriers (parents of BBS patients) were heterozygous for the variant, and no unaffected individuals were homozygous for the variant.

The detection of mutations in the two BBS2 families prompted the inventors to sequence the NGVN gene from a panel of 18 unrelated BBS probands in an attempt to identify additional mutations in NGVN. A 1 bp insertion (1206insA) was observed in exon 10 in the homozygous state in a single proband (BB31-1). The insertion results in a frameshift that predicts premature termination of translation five amino acids downstream from the insertion. One proband harbored an exon 8 nonsense mutations at codon 275 (Arg275Stp) in the homozygous state. A second exon 8 nonsense mutation (Arg272Stp) was found in the heterozygous state in another proband. In all, mutations were observed in 3 of 18 unrelated BBS probands.

In addition to the mutations described above, other sequence variants were found that are likely to be benign sequence variations. The conservative Ile123Val change was found in the heterozygous state in two of the probands (BBI-1 and BB55-1) as well as in control individuals. Furthermore, an A1413C transversion resulting in a synonymous codon change was observed in one proband (BB55-1).

Evolutionary Conservation

Homology screening of NGVN against the public sequence databases demonstrates that NGVN has strong sequence homology to genes from a number of other organisms. Sequence for the mouse orthologue for NGVN was obtained by PCR from a 17 day fetal mouse cDNA library to supplement the sequence that was available from GenBank. The mouse gene is 90% identical and 95% similar to the human gene within the coding region at the protein level. Sequence for the rat and zebrafish orthologues of NGVN were obtained using the same methodology as was employed to ascertain the sequence for the mouse orthologue. The rat orthologue was found to be 89% identical and 94% similar at the protein level. The zebrafish orthologue was found to be 74% identical and 84% similar. A reduced level of homology was found for organisms such as *C. elegans, Chlamydomonas* and *Trypanosoma* (30 to 46% identical; 49 to 57% similar).

In order to further investigate the disease causing nature of the exon 2 Val75Gly variant, sequence was obtained from a number of organisms to determine the level of sequence conservation within this region. Valine was found at this position in human, bovine, rabbit, rat, mouse and zebrafish. In *C. elegans, Trypanosoma* and *Chlamydomonas*, the conservative substitution of isoleucine was found at this position. There is a high level of conservation at a number of locations within this region as well as within the region surrounding the Ile75Val variant in exon 3. However, the isoleucine at codon 123 shows a lower level of conservation, consistent with its postulated assignment as a likely benign sequence variant.

Lack of Homology to MKKS and Other Known Genes

As the BBS6 gene, MKKS, has been provisionally identified as a chaperonin, the inventors attempted to identify homology between NGVN and known chaperonin or chaperonin-like genes. No homology was found to any genes with known function by both BLAST analysis or by searching for functional domains within NGVN.

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,664,911
U.S. Pat. No. 4,683,195
U.S. Pat. No. 4,683,202
U.S. Pat. No. 4,786,600
U.S. Pat. No. 4,792,447
U.S. Pat. No. 4,800,159
U.S. Pat. No. 4,873,191
U.S. Pat. No. 4,883,750
U.S. Pat. No. 4,946,773
U.S. Pat. No. 4,988,617
U.S. Pat. No. 5,712,097
U.S. Pat. No. 5,045,451
U.S. Pat. No. 5,190,856
U.S. Pat. No. 5,270,184
U.S. Pat. No. 5,279,721
U.S. Pat. No. 5,324,631
U.S. Pat. No. 5,494,810
U.S. Pat. No. 5,496,699
U.S. Pat. No. 5,578,706
U.S. Pat. No. 5,633,365
U.S. Pat. No. 5,639,611
U.S. Pat. No. 5,665,549
U.S. Pat. No. 5,686,072
U.S. Pat. No. 5,712,124
U.S. Pat. No. 5,733,733
U.S. Pat. No. 5,733,752
U.S. Pat. No. 5,744,311
U.S. Pat. No. 5,747,255
U.S. Pat. No. 5,767,072
GB Application 2 202 328
EPO No. 320 308,
EPO No. 329 822,
PCT/US87/00880
PCT/US89/01025
WO 84/03564
WO 88/10315
WO 89/06700
WO 90/07641
Arcone, et al., *Nucl. Acids Res.*, 16(8): 3195-3207, 1988.
Baichwal and Sugden, In: *Gene Transfer*, pp. 117-148, 1986.
Barany and Merrifield, *The Peptides*, pp. 1-284, 1979.
Bartlett et al., *Proc. Nat'l Acad. Sci. USA*, 93:8852-8857, 1996.
Beales et al., *Nephrology Dialysis Transplantation* 15 (12): 1977-1985, 2000.
Benveniaty and Neshif, *Proc. Nat'l Acad. Sci. USA*, 83:9551-9555, 1986.
Brinster et al., *Proc. Nat'l Acad. Sci. USA*, 82: 4438-4442, 1985.
Campbell, In: *Monlclonal Antibody Technolgoy, Laboratory Techniques in Biochemistry and Molecular Biology*, Vol. 13, pp. 75-83, Amsterdam, Elseview, 1984.
Capaldi et al., *Biochem. Biophys. Res. Comm.*, 76:425, 1977
Carter and Flotte, *Ann. N.Y. Acad. Sci.*, 770:79-90, 1995.
Chatterjee, et al., *Ann. N.Y. Acad. Sci.*, 770:79-90, 1995.
Chen and Okayama, *Mol. Cell. Biol.*, 7:2745-2752, 1987.
Coffin, In: *Virology*, ed., New York: Raven Press, pp. 1437-1500, 1990.
Coupar et al., *Gene*, 68:1-10, 1988
Davey et al., EPO No. 329 822.
Dubensky et al., *PROc. Nat'l Acad. Sci. USA*, 81:7529-7533, 1984.
Fechheimer et al, *PROc. Nat'l Acad. Sci. USA*, 84:8463-8467, 1987.
Ferkol et al., *FASEB J*, 7:1081-1091, 1993.
Ferrari et al., *J. Virol.*, 70:3227-3234, 1996.
Fisher et al., *J. Virol.*, 70:520-532, 1996.
Flotte et al., *PROC. Nat'l Acad. Sci. USA*, 90:10613-10617, 1993.
Fodor et al., *SCIENce*, 251:767-773, 1991.
Fraley et al., *PROC. Nat'l Acad. Sci. USA*, 76:3348-3352, 1979.
Freifelder, *Physical Biochemistry Applications to Biochemistry and Molecular Biology*, 2nd ed., 1982.
Ghosh and Bachhawat, In: *Liver Diseases, Targeted Diagnosis and Therapy Using Specific Receptors and Ligands.* Wu et al, pp. 87-104, 1991.
Gingeras et al., PCT Application WO 88/10315,
Goding, 1986, In: *Monoclonal Antibodies: Principles and Practice*, pp. 60-61, and 71-74, 1986.
Goodman et al., *Blood*, 84:1492-1500, 1994.
Gopal, *Mol. Cell. Biol.*, 5:1188-1190, 1985.
Gossen and Bujard, *Proc. Nat'l Acad. Sci. USA*, 89:5547-5551, 1992.
Gossen et al., *Science*, 268:1766-1769, 1995.
Graham and van der Eb, *Virology*, 52:456-467, 1973.
Hacia et al., *Nature Genetics*, 14:441-447, 1996.
Harland and Weintraub, *J. Cell Biol.*, 101:1094-1099, 1985.
Hay et al., *J. Mol. Biol.*, 175:493-510, 1984.
Hearing and Shenk, *J. Mol. Biol.* 167:809-822, 1983.
Hearing et al., *J. Virol.*, 67:2555-2558, 1987.
Hudson et al., *Science* 270: 1945-1954, 1995.
Johnson et al., Peptide Turn Mimetics" In: *Biotechnology And Pharmacy*, 1993.
Joki et al., *Human Gene Ther.*, 6:1507-1513, 1995.
Kageyama et al., *J. Biol. Chem.*, 262(5):2345-2351, 1987,
Kaneda et al, *Science*, 243:375-378, 1989.
Kaplitt et al., *Nat'l Genet.*, 8:148-153, 1994.
Kato et al, *J. Biol. Chem.*, 266:3361-3364, 1991.

Kessler et al., *Proc. Nat'l Acad. Sci. USA*, 93:14082-14087, 1996.
Klein et al., *Nature*, 327:70-73, 1987.
Koeberl et al., *Proc. Nat'l Acad Sci. USA*, 94:1426-1431, 1997.
Kohler and Milstein, *Eur. J. Immunol.*, 6:511-519, 1976.
Kwoh et al., *Proc. Nat'l Acad. Sci. USA*, 86: 1173, 1989.
Levrero et al., *Gene*, 101:195-202, 1991.
Mann et al., *Cell*, 33:153-159, 1983.
McCown et al., *Brain Res.*, 713:99-107, 1996.
Merrifield, *Science*, 232: 341-347, 1986.
Miller et al., PCT Application WO 89/06700
Mizukami et al., *Virology*, 217:124-130, 1996.
Myers, EPO 0273085
Nakamura et al., In: *Handbook of Experimental Immunology* (4th Ed.), 1987.
Newton 1989.
Nicolas and Rubenstein, In: *Vectors: A survey of molecular cloning vectors and their uses*, pp. 493-513, 1988,
Nicolau and Sene, *Biochim. Biophys. Acta*, 721:185-190, 1982,
Nicolau et al., *Methods Enzymol.*, 149:157-176, 1987.
Olivierio et al., *EMBO J.*, 6(7):1905-1912, 1987.
Paskind et al., *Virology*, 67:242-248, 1975.
Pease et al., *Proc. Nat'l Acad. Sci. USA*, 91:5022-5026, 1994.
Perales et al., *Proc. Nat'l Acad. Sci.* 91:4086-4090, 1994.
Pignon et al., *Hum. Mutat.*, 3: 126-132, 1994.
Ping et al., *Microcirculation*, 3:225-228, 1996.
Poli and Cortese, *Proc. Nat'l Acad. Sci. USA*, 86:8202-8206, 1989.
Potter et al., *Proc. Nat'l Acad. Sci. USA*, 81:7161-7165, 1984.
Prowse and Baumann, *Mol Cell Biol*, 8(1):42-51, 1988.
Radler et al., *Science*, 275:810-814, 1997.
Renan, *Radiother. Oncol.*, 19:197-218, 1990.
Ridgeway, In: *Vectors: A survey of molecular cloning vectors and their uses*, pp. 467-492, 1988.
Rippe et al., *Mol. Cell. Biol.*, 10:689-695, 1990.
Ron, et al., *Mol. Cell. Biol.*, 2887-2895, 1991.
Roux et at, *Proc. Nat'l Acad. Sci. USA*, 86:9079-9083, 1989.
Sambrook et al., In: *Molecular Cloning: A Laboratory Manual*, 1989.
Samulski et al., *J. Virol.*, 61(10):3096-3101, 1987.
Shoemaker et al., *Nature Genetics* 14:450-456, 1996.
Stewart and Young, Solid Phase Peptide Synthesis, 2d. ed., Pierce Chemical Co., 1984.
Takagi et al., *Gastroenterology*, 111:1369, 1996.
Tam et al., *J. Am. Chem. Soc.*, 105:6442, 1983.
Temin, In: *Gene Transfer*, Kucherlapati (ed.), New York: Plenum Press, pp. 149-188, 1986.
Tibbetts *Cell*, 12:243-249, 1977.
Tur-Kaspa et al., *Mol. Cell. Biol.*, 6:716-718, 1986.
Wagner et al., *Proc. Nat'l Acad. Sci.* 87, 9:3410-3414, 1990.
Walker et al., *Proc. Nat'l Acad. Sci. USA*, 89:392-396 1992.
Walther and Stein, *J. Mol. Med.*, 74:379-392, 1996.
Watt et al., *Proc. Nat'l Acad. Sci.*, 83(2): 3166-3170, 1986.
Wilson et al., *Mol. Cell. Biol.*, 6181-6191, 1990.
Wong et al., *Gene*, 10:87-94, 1980.
Wu and Wu, *Adv. Drug Delivery Rev.*, 12:159-167, 1993.
Wu and Wu, *J. Biol. Chem.*, 262:4429-4432, 1987.
Wu and Wu, *Biochem.*, 27:887-892, 1988.
Wu et al., *Genomics*, 4:560, 1989.
Xiao et al., *J. Virol.*, 70:8098-8108, 1996.
Yang et at, *Proc. Nat'l Acad. Sci. USA*, 87:9568-9572, 1990.
Zechner et al., *Mol. Cell. Biol.*, 2394-2401, 1988.

---

What is claimed is:

1. An isolated and purified nucleic acid encoding a human negevin (NGVN) polypeptide, wherein the polypeptide comprises SEQ ID NO: 2 or a variant thereof comprising one or more of the following changes: Val175Gly, Arg272Stp, Ile123Val, or a frameshift starting at residue 314 or residue 403 of SEQ ID NO:2 and which hybridize to a nucleic acid encoding SEQ ID NO:2 under high stringency conditions.

2. The nucleic acid of claim 1, wherein said polypeptide comprises the sequence of SEQ ID NO:2 wherein said nucleic acid comprises the sequence of SEQ ID NO:1 or SEQ ID NO: 3.

3. The nucleic acid of claim 1, wherein the nucleic acid comprises the sequence of SEQ ID NO:1 or SEQ ID NO:3 or one or more of the changes selected from the group consisting of $T_{224} \rightarrow G$, $C_{814} \rightarrow T$, $C_{823} \rightarrow T$, $A_{367} \rightarrow G$, $A_{1413} \rightarrow C$, $A_{940}$del and 1206insA of SEQ ID NO:1.

4. The nucleic acid of claim 1, wherein the nucleic acid comprises the sequence of SEQ ID NO:3 except for one or one or more of the changes selected from the group consisting of $T_{224} \rightarrow G$, $C_{814} \rightarrow T$, $C_{823} \rightarrow T$, $A_{387} \rightarrow G$, $A_{1413} \rightarrow C$, $A_{940}$del and 1206insA.

5. The nucleic acid of claim 1, further comprising a promoter.

6. The nucleic acid of claim 5, wherein said promoter is selected from the group consisting of an inducible promoter, a constitutive promoter, and a tissue specific promoter.

7. The nucleic acid of claim 5, wherein said promoter is active in eukaryotic cells.

8. The nucleic acid of claim 5, further comprising a selectable marker.

9. The nucleic acid of claim 5, further comprising a polyadenylation signal.

10. The nucleic acid of claim 5, further comprising an origin of replication.

11. The nucleic acid of claim 10, wherein said nucleic acid is part of a replicable vector.

12. The nucleic acid of claim 11, wherein said vector is a viral vector.

13. The nucleic acid of claim 12, wherein said viral vector is selected from the group consisting of a retroviral vector, an adenoviral vector, an adeno-associated viral vector, a herpes viral vector, a polyoma viral vector, a vaccinia viral vector and a lentiviral vector.

14. The nucleic acid of claim 12, wherein said viral vector is located within a viral particle.

15. The nucleic acid of claim 10, wherein said vector is a non-viral vector.

* * * * *

UNITED STATES PATENT AND TRADEMARK OFFICE
CERTIFICATE OF CORRECTION

| | | |
|---|---|---|
| PATENT NO. | : 8,129,161 B2 | Page 1 of 1 |
| APPLICATION NO. | : 12/908707 | |
| DATED | : March 6, 2012 | |
| INVENTOR(S) | : Val Sheffield et al. | |

It is certified that error appears in the above-identified patent and that said Letters Patent is hereby corrected as shown below:

In column 1, lines 14-15, delete paragraph and insert
--This invention was made with government support under grant number R01-EY-11298 awarded by the National Institutes of Health. The government has certain rights in the invention.-- therefor.

Signed and Sealed this
Fifteenth Day of May, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,129,161 B2 |
| APPLICATION NO. | : 12/908707 |
| DATED | : March 6, 2012 |
| INVENTOR(S) | : Val Sheffield, Darryl Nishimura and Edwin Stone |

It is certified that error appears in the above-identified patent and that said Letters Patent is hereby corrected as shown below:

In the Specification

Column 1, Line 15:
Delete "R01-EY-11298" and replace with -- EY011298 --.

Signed and Sealed this
Third Day of January, 2023

Katherine Kelly Vidal
*Director of the United States Patent and Trademark Office*